United States Patent
Simon et al.

(10) Patent No.: US 8,401,650 B2
(45) Date of Patent: *Mar. 19, 2013

(54) METHODS AND APPARATUS FOR ELECTRICAL TREATMENT USING BALLOON AND ELECTRODE

(75) Inventors: Bruce Simon, Mountain Lakes, NJ (US); Steven Mendez, Chester, NJ (US); Hecheng Hu, Cedar Grove, NJ (US); Richard P. Dickerson, Rockaway, NJ (US); James R. Pastena, Succasunna, NJ (US); Puyun Guo, Summit, NJ (US)

(73) Assignee: ElectroCore LLC, Morris Plains, NJ (US)

( * ) Notice: Subject to any disclaimer, the term of this patent is extended or adjusted under 35 U.S.C. 154(b) by 1020 days.

This patent is subject to a terminal disclaimer.

(21) Appl. No.: 12/394,972

(22) Filed: Feb. 27, 2009

(65) Prior Publication Data

US 2009/0259274 A1 Oct. 15, 2009

Related U.S. Application Data

(63) Continuation-in-part of application No. 12/338,191, filed on Dec. 18, 2008, now Pat. No. 8,209,034.

(60) Provisional application No. 61/043,802, filed on Apr. 10, 2008, provisional application No. 61/043,805, filed on Apr. 10, 2008.

(51) Int. Cl.
*A61N 1/00* (2006.01)
(52) U.S. Cl. .................................................. 607/40
(58) Field of Classification Search ...................... 607/40
See application file for complete search history.

(56) References Cited

U.S. PATENT DOCUMENTS

| 4,198,936 A | 4/1980 | Pagel et al. |
| 4,304,239 A | 12/1981 | Perlin |

(Continued)

FOREIGN PATENT DOCUMENTS

| WO | 0100273 | 1/2001 |
| WO | 2005007120 | 1/2005 |

OTHER PUBLICATIONS

International Search Report and Written Opinion for Corresponding PCT Application PCT/US09/36259, May 11, 2009.

*Primary Examiner* — George Manuel
*Assistant Examiner* — Robert N Wieland
(74) *Attorney, Agent, or Firm* — Jospeh P Errico

(57) ABSTRACT

The present invention provides systems, apparatus and methods for selectively applying electrical energy to body tissue. A device is provided having an enclosure within an outer wall formed from an electrically-permeable material to allow for electrical energy to pass from the interior of the enclosure through the outer wall. The device further includes an electrode positioned within the interior of the enclosure and a fluid passage coupled to the enclosure for delivery of an electrically conductive fluid into the interior of the enclosure such that the electrically conductive fluid couples the electrode with the electrically-permeable section of the outer wall. The conductive fluid allows for the passage of electrical energy from the electrode through the fluid and the outer wall of the enclosure for treatment of tissue on or in a patient. In this manner, the electrode does not directly contact the tissue of the patient, which reduces the potential for collateral tissue damage or necrosis and/or excessive electric fields in the tissue.

38 Claims, 10 Drawing Sheets

U.S. PATENT DOCUMENTS

| | | |
|---|---|---|
| 4,351,330 A | 9/1982 | Scarberry |
| 4,574,807 A | 3/1986 | Hewson et al. |
| 4,640,298 A | 2/1987 | Pless et al. |
| 4,706,688 A | 11/1987 | Don Michael et al. |
| 4,817,611 A | 4/1989 | Arzbaecher et al. |
| 4,919,147 A | 4/1990 | Reinhardt et al. |
| 5,003,991 A | 4/1991 | Takayama et al. |
| 5,056,532 A | 10/1991 | Hull et al. |
| 5,249,585 A | 10/1993 | Turner et al. |
| 5,366,490 A | 11/1994 | Edwards et al. |
| 5,370,675 A | 12/1994 | Edwards et al. |
| 5,370,679 A | 12/1994 | Atlee, III |
| 5,431,696 A | 7/1995 | Atlee, III |
| 5,505,700 A * | 4/1996 | Leone et al. ............. 604/101.03 |
| 5,540,730 A | 7/1996 | Terry, Jr. et al. |
| 5,626,618 A | 5/1997 | Ward et al. |
| 5,692,506 A | 12/1997 | Linder |
| 5,707,400 A | 1/1998 | Terry, Jr. et al. |
| 5,800,378 A | 9/1998 | Edwards et al. |
| 5,967,977 A | 10/1999 | Mullis et al. |
| 6,006,138 A | 12/1999 | Don Michael |
| 6,083,249 A | 7/2000 | Familoni |
| 6,083,255 A | 7/2000 | Laufer et al. |
| 6,148,222 A | 11/2000 | Ramsey, III |
| 6,198,970 B1 | 3/2001 | Freed et al. |
| 6,327,503 B1 | 12/2001 | Familoni |
| 6,341,236 B1 | 1/2002 | Osorio et al. |
| 6,347,247 B1 | 2/2002 | Dev et al. |
| 6,356,786 B1 | 3/2002 | Rezai et al. |
| 6,356,787 B1 | 3/2002 | Rezai et al. |
| 6,366,814 B1 | 4/2002 | Boveja et al. |
| 6,423,058 B1 | 7/2002 | Edwards et al. |
| 6,425,877 B1 | 7/2002 | Edwards |
| 6,438,423 B1 | 8/2002 | Rezai et al. |
| 6,609,030 B1 | 8/2003 | Rezai et al. |
| 6,610,713 B2 | 8/2003 | Tracey |
| 6,656,960 B2 | 12/2003 | Puskus |
| 6,778,854 B2 | 8/2004 | Puskus |
| 6,819,956 B2 | 11/2004 | DiLorenzo |
| 6,865,416 B2 | 3/2005 | Dev et al. |
| 6,871,092 B2 | 3/2005 | Piccone |
| 6,885,888 B2 | 4/2005 | Rezai |
| 6,934,583 B2 | 8/2005 | Weinberg et al. |
| 6,937,896 B1 | 8/2005 | Kroll |
| 6,955,173 B2 | 10/2005 | Lesh |
| 6,980,865 B1 | 12/2005 | Wang et al. |
| 7,008,419 B2 | 3/2006 | Shadduck |
| 7,043,307 B1 | 5/2006 | Zelickson et al. |
| 7,072,720 B2 | 7/2006 | Puskus |
| 7,081,115 B2 * | 7/2006 | Taimisto ........................ 606/41 |
| 7,142,910 B2 | 11/2006 | Puskas |
| 7,167,750 B2 | 1/2007 | Knudson et al. |
| 7,229,469 B1 | 6/2007 | Witzel et al. |
| 7,292,890 B2 | 11/2007 | Whitehurst et al. |
| 7,310,552 B2 | 12/2007 | Puskas |
| 7,326,207 B2 | 2/2008 | Edwards |
| 7,400,929 B2 | 7/2008 | Zelickson et al. |
| 8,150,520 B2 * | 4/2012 | Demarais et al. ............... 607/44 |
| 2001/0031941 A1 | 10/2001 | Edwards et al. |
| 2002/0010495 A1 | 1/2002 | Freed et al. |
| 2002/0016344 A1 | 2/2002 | Tracey |
| 2002/0016615 A1 | 2/2002 | Dev |
| 2002/0116030 A1 | 8/2002 | Rezai |
| 2002/0183682 A1 | 12/2002 | Darvish et al. |
| 2002/0198570 A1 | 12/2002 | Puskas |
| 2003/0009208 A1 | 1/2003 | Snyder et al. |
| 2003/0074039 A1 | 4/2003 | Puskas |
| 2003/0195593 A1 | 10/2003 | Ingle et al. |
| 2004/0039431 A1 | 2/2004 | Machold et al. |
| 2004/0059383 A1 | 3/2004 | Puskas |
| 2004/0172075 A1 | 9/2004 | Shafer et al. |
| 2004/0249416 A1 | 12/2004 | Yun et al. |
| 2005/0021092 A1 | 1/2005 | Yun et al. |
| 2005/0065553 A1 | 3/2005 | Ben Ezra et al. |
| 2005/0065562 A1 | 3/2005 | Rezai |
| 2005/0065573 A1 | 3/2005 | Rezai |
| 2005/0075701 A1 | 4/2005 | Shafer |
| 2005/0075702 A1 | 4/2005 | Shafer |
| 2005/0125044 A1 | 6/2005 | Tracey |
| 2005/0143412 A1 | 6/2005 | Puskas |
| 2005/0149146 A1 | 7/2005 | Boveja et al. |
| 2005/0153885 A1 | 7/2005 | Yun |
| 2005/0165388 A1 | 7/2005 | Bhola |
| 2005/0182463 A1 | 8/2005 | Hunter et al. |
| 2005/0216062 A1 | 9/2005 | Herbst |
| 2005/0240241 A1 | 10/2005 | Yun |
| 2005/0256028 A1 | 11/2005 | Yun |
| 2005/0273146 A1 | 12/2005 | DeSimone et al. |
| 2006/0129215 A1 | 6/2006 | Helmus et al. |
| 2006/0135998 A1 | 6/2006 | Libbus et al. |
| 2006/0167498 A1 | 7/2006 | DiLorenzo |
| 2006/0259107 A1 | 11/2006 | Caparso et al. |
| 2007/0106337 A1 | 5/2007 | Errico et al. |
| 2007/0106338 A1 | 5/2007 | Errico |
| 2007/0106339 A1 | 5/2007 | Errico et al. |
| 2007/0191902 A1 | 8/2007 | Errico et al. |
| 2007/0213645 A1 | 9/2007 | Zumeris et al. |
| 2007/0225768 A1 | 9/2007 | Dubak |
| 2008/0039904 A1 | 2/2008 | Bulkes et al. |
| 2008/0300571 A1 * | 12/2008 | LePivert ........................ 604/503 |

* cited by examiner

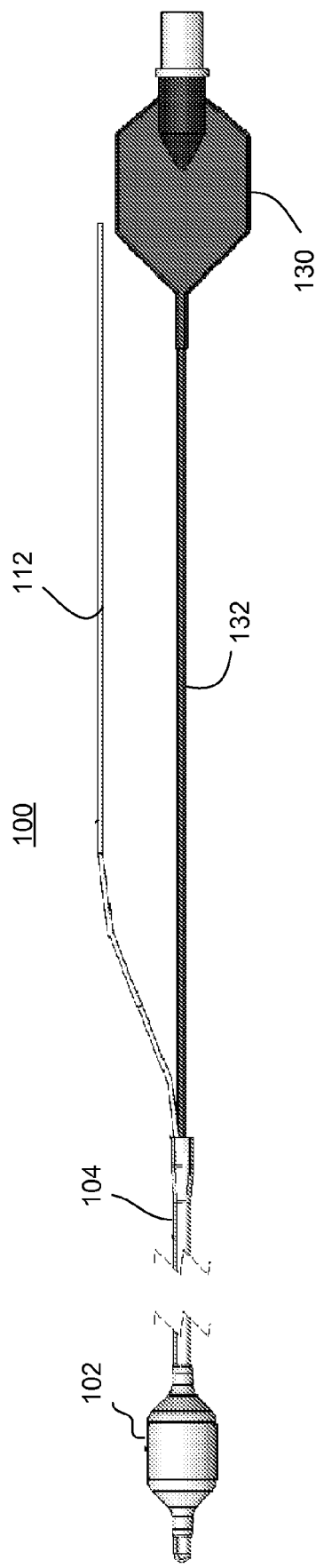
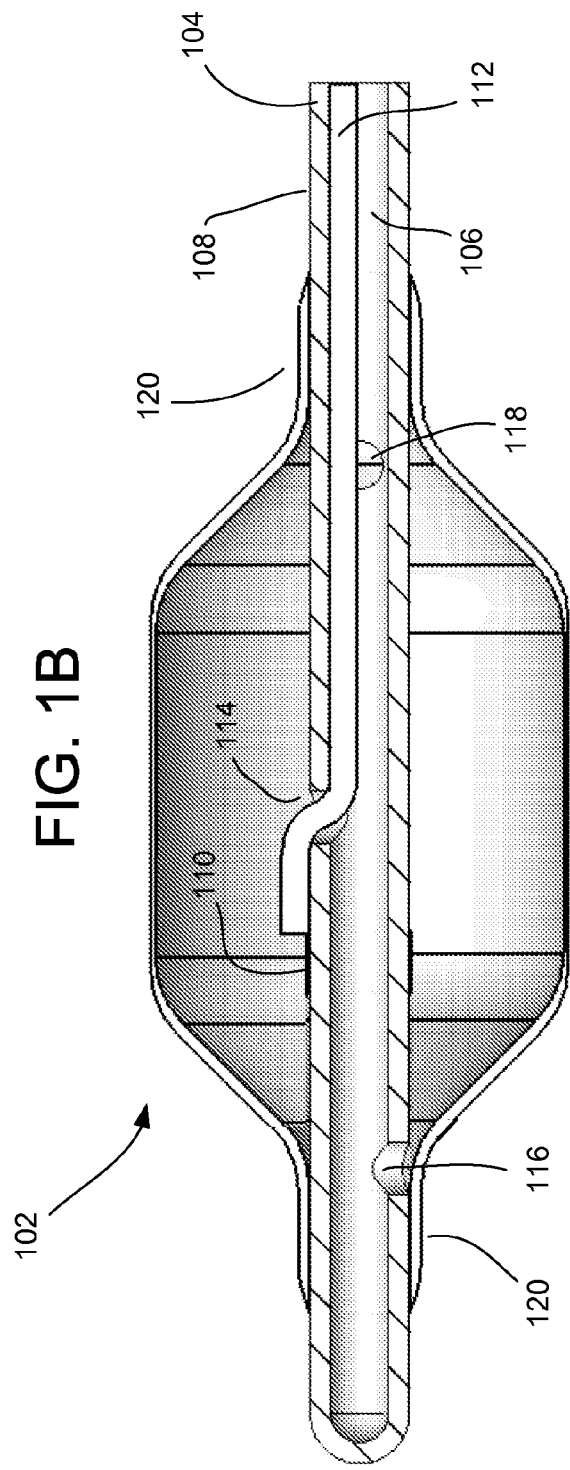
FIG. 1A
FIG. 1B

METHODS AND APPARATUS FOR
ELECTRICAL TREATMENT USING
BALLOON AND ELECTRODE

CROSS REFERENCE TO RELATED APPLICATIONS

The present application is a continuation-in-part of U.S. patent application Ser. No. 12/338,191, filed Dec. 18, 2008, now pending, and claims the benefit of U.S. provisional patent application Ser. No. 61/043,805, filed Apr. 10, 2008, and 61/043,802, filed Apr. 10, 2008, where the entire disclosures of all of the above applications are incorporated herein by reference for all purposes.

This application is also related to commonly assigned co-pending U.S. patent Ser. Nos. 11/555,142, 11/555,170, 11/592,095, 11/591,340, 11/591,768, 11/754,522, 11/735,709 and 12/246,605, the entire disclosures of which are incorporated herein by reference for all purposes.

BACKGROUND OF THE INVENTION

The present invention relates to the delivery of electrical energy to bodily tissues for therapeutic purposes, and more specifically to devices and methods for treating conditions through delivery of electrical energy using a balloon and electrode device.

The use of electrical stimulation for treatment of medical conditions has been well known in the art for nearly two thousand years. It has been recognized that electrical stimulation of the brain and/or the peripheral nervous system and/or direct stimulation of the malfunctioning tissue, which stimulation is generally a wholly reversible and non-destructive treatment, holds significant promise for the treatment of many ailments.

One of the most successful modern applications of the relationship between muscle and nerves is the cardiac pacemaker. Although its roots extend back into the 1800's, it was not until 1950 that the first practical, albeit external and bulky pacemaker was developed. Dr. Rune Elqvist developed the first truly functional, wearable pacemaker in 1957. Shortly thereafter, in 1960, the first fully implanted pacemaker was developed.

Among the developments in the treatment of patients with heart ailments has been the introduction of electrodes for electrical stimulation through the esophagus. For example, esophageal stimulation and monitoring leads are known in the art, adapted specifically for cardiac pacing, as disclosed in U.S. Pat. Nos. 4,574,807; 4,198,936; and 4,706,688, the entire disclosures of which are hereby incorporated by reference herein. Typically, esophageal pacing leads include one or more balloons, adapted to stabilize the location of the lead in the esophagus. In some cases, the electrodes are located on the balloon, as in U.S. Pat. No. 4,198,936. In other cases, the electrodes are located proximal or distal to the balloon as in U.S. Pat. No. 4,574,807. In some other cases, the balloon is arranged eccentrically, and is used both to stabilize the lead and urge the electrodes into contact with the anterior inner surface of the esophagus, as in U.S. Pat. No. 4,706,688.

More specifically, U.S. Pat. No. 4,706,688 discloses a device 10 inserted into the esophagus 34 of a patient. The device 10 is inserted through the nasal region 32, through the esophagus 34 and into the stomach 36. Once the device 10 has been inserted, fluid is caused to flow along airway 24 such that a balloon cuff 18 expands. The purpose of cuff 18 is to locate the gastroesophageal junction just proximate to the cuff 18. A second balloon cuff 20 is located posterior to the heart region 40 such that when it is expanded, at least some of the electrodes 26 abut against the esophagus 34 adjacent the heart 40.

U.S. Pat. No. 5,056,532 discloses a lead having an elongated flexible lead body 10, which is provided with three longitudinal lumens. At the distal end of the lead a balloon 12 is mounted around the external surface of the lead body 10. Proximal to balloon 12 is a second balloon 20. An electrode lead 24 is slideably mounted within a lumen within lead body 10, and ventricular electrodes 26 and 28 are mounted to lead 24. The electrode lead 24 and electrodes 26 and 28 may be slideably adjusted relative to the position of balloon 20. A third balloon 30 is located proximal to balloon 20. Atrial electrodes 34 and 36 are located on electrode lead 24, such that movement of lead 24 within the lead body 10 adjusts the positions of electrodes 34 and 36 relative to balloon 30.

The lead is advanced through the mouth or the nasal cavity, down the esophagus until the distal end 18 of the lead is well within the stomach. The balloon 12 is then inflated, and the lead is withdrawn until balloon 12 lies against the gastroesophageal junction. Balloons 20 and 30 are then inflated, urging electrode lead 24 against the anterior inner surface of the esophagus, closest to the heart. Notably, when the balloons 20 and 30 are inflated, electrodes 26 and 28 and electrodes 34 and 36 are urged into contact with the anterior inner surface of the esophagus.

It has been discovered that the above esophageal electrode and balloon configurations are not satisfactory for all applications. Accordingly, there is a need in the art for new products and methods for treating conditions through delivery of electromagnetic impulses using balloon electrodes.

SUMMARY OF THE INVENTION

The present invention provides systems, apparatus and methods for selectively applying electrical energy to body tissue. In one aspect of the invention, a device is provided having an enclosure with an outer wall having at least one section that is formed from an electrically-permeable material to allow for electrical energy to pass from the interior of the enclosure through the outer wall. The device further includes at least one electrode positioned within the interior of the enclosure and a fluid passage coupled to the enclosure for delivery of an electrically conductive fluid into the interior of the enclosure such that the electrically conductive fluid couples the electrode(s) with the electrically-permeable section of the outer wall. The conductive fluid allows for the passage of electrical energy from the electrode through the fluid and the outer wall of the enclosure for treatment of tissue on or in a patient.

One of the key advantages of the present invention is that the electrode does not directly contact the tissue of the patient, which reduces the potential for collateral tissue damage or necrosis and/or excessive electric fields in the tissue. In addition, the enclosure physically shields the electrode from the patient's tissue which substantially inhibits Faradic products (e.g., OH$^-$, H$_2$O$_2$) of the electrode from reaching the target site. In this manner, a direct or low frequency current can be applied to the electrode(s) without the danger of such Faradic products reaching excessively high concentrations at the tissue site. In addition, the direct or low frequency current can be delivered for a longer period of time and/or at higher power levels than is conventionally considered safe, which allows for the invention to be used in a variety of applications as described in more detail below and as will be understood by those of skill in the art.

In a preferred embodiment, the enclosure is a balloon that is movable from a deflated position for introduction into a patient to an inflated position wherein at least a portion of the outer wall of the balloon contacts target tissue within the patient. The balloon is preferably inflated by introducing an electrically conductive fluid into the balloon. The conductive fluid serves to inflate the balloon to allow the balloon to contact target tissue, and to electrically couple the electrode to the outer wall of the balloon. The material of the balloon is preferably very soft and flexible, e.g., elastic, such that it gently conforms to the surrounding tissue, which allows the electrically energy to be applied uniformly to the target tissue. In addition, one skilled in the art will recognize that this configuration allows the balloon to conform to a variety of different tissue shapes and structures within the patient's body. Another advantage of the invention is that the balloon, in the inflated position, has a larger tissue contact area than the electrode, which allows the device to be applied to a larger tissue treatment area. This can be particularly advantageous when the device is introduced to the tissue treatment area endoscopically or percutaneously as the balloon can be introduced into the patient in the deflated position and then inflated to contact a larger tissue area.

In another aspect of the invention, the device includes an introducer for introducing the device to a target location within the patient. The electrode and the balloon are coupled to a distal portion of the introducer. In a preferred embodiment, the electrode is coupled to the introducer such that, when the balloon is inflated, the electrode is substantially centrally located within the interior of the balloon. This configuration ensures that the electrode is spaced sufficiently from the patient's tissue to minimize tissue necrosis and collateral tissue damage. In certain embodiments, the introducer is an NG tube designed for passage through the patient's esophagus to a target location therein, such as the vagus nerve. In other embodiments, the introducer may be an endotracheal tube designed for passage through the patient's trachea or a percutaneous introducer designed for percutaneous penetration into the patient, e.g., to the epidural space of a patient.

In a particularly preferred embodiment, the balloon is formed substantially from an ion-permeable and/or hydrophilic material. As the balloon is filled with a conductive fluid, such as saline, the outer surface of the balloon wets and permits good contact with the surrounding tissue of the patient, which may otherwise be dry. In certain embodiments, the balloon may include one or more sections formed from an ion-permeable material with other sections formed from an electrically insulating material, or the entire wall of the balloon may be formed from such a material. In the former embodiment, the balloon may be constructed to selectively apply electrical energy through certain sections of its outer wall to selectively apply such energy to specific tissue locations on the body. In the latter embodiment, the electrical energy will preferably be distributed substantially evenly through the entire outer wall of the balloon.

Preferably, electrical properties of the electrode, the fluid, and the material of the balloon are such that a resistance through the electrode, the fluid, and the balloon outer wall is less than about 1,000 Ohms, more preferably less than about 400 Ohms, and preferably less than 200 Ohms. In one embodiment, the return electrode is a return pad located on a surface of the patient's skin, such as the back or hip, and the electrode within the balloon acts as the tissue treatment or active electrode. In this embodiment, an electromagnetic field emanates from the active electrode through the tissue in a substantially radial pattern. In alternative embodiments, the return electrode may be located closer to the active electrode, e.g., within the balloon, coupled to the introducer outside of the balloon or within a second balloon. In these embodiments, the electrical energy will not flow completely through the patient's body, i.e., the current will generally flow from the active electrode through the conductive fluid and the outer wall of the balloon, through the patient's tissue at the target site and to the return electrode.

In one embodiment, the device further includes a vacuum source for aspirating the electrically conductive fluid from the interior of the balloon. The vacuum source may be a positive source of aspiration with an aspiration passage coupled to the interior of the balloon or the device may be designed to simply allow the fluid to evacuate the balloon through the same fluid passage it entered through pressure differential, gravity, or the like. Evacuating the conductive fluid deflates the balloon and allows any excess Faradic products and/or heat to be evacuated from the device. In this manner, the balloon may be periodically evacuated to allow for periodic evacuation of excess Faradic products and heat, which allows for higher power levels and/or longer continuous use of the device in the patient. In some embodiments, the device may be adapted for continuous circulation of the electrically conductive fluid to reduce any build-up of heat or Faradic products and ensure uniform temperatures at the outer surface of the balloon. These embodiments will allow the device to use much higher power levels as the heat generated around the electrode and within the conductive fluid from the higher power levels will be continuously evacuated from the interior of the balloon.

In one embodiment, the outer wall of the balloon is formed from a stretchable elastic material permitting the interior of the balloon to accommodate a variable volume of fluid ranging from a minimum deflated volume to a maximum inflated volume. The wall provides the balloon with an inflated shape within a body cavity or other target area within a patient approximating the shape of the body cavity or other target area. The elastic material of the balloon will preferably allow the outer wall of the balloon to conform to the tissue surrounding the body cavity or target area within the patient's body. Alternatively, the balloon may be designed to inflate to a pre-formed shape corresponding to a targeted area within a patient.

In an alternative embodiment, the balloon has at least one section of its outer wall formed of a semi-permeable material that will permit the passage of certain compounds. For example, the balloon may be formed of a material having a pore size that will permit the passage of certain drugs, such as anti-cancer agents, through the outer wall of the balloon. In this manner, the balloon may act as a drug-delivery device by introducing one or more drugs into the conductive fluid and permitting the drug(s) to pass through the balloon and into the tissue. Moreover, the device may be used to time-release the drugs into the patient's tissue. In one embodiment, the conductive fluid is continuously circulated through the interior of the balloon to precisely control the dosage of drugs delivered into the patient over a period of time. In alternative embodiments, the material of the balloon is designed to allow passage of the drugs over a period of time.

In an alternative embodiment, a system is provided for delivering electrical energy to tissue within a patient. The system includes a source of electrical energy coupled to an enclosure, such as a balloon, and a fluid delivery system for delivering electrically conductive fluid to the interior of the enclosure. In this embodiment, the system does not include an active or tissue treatment electrode. The electrically conductive fluid serves to inflate the balloon for contacting tissue and also serves as the active or tissue treatment electrode. The system may also include a return electrode coupled to the source of electrical energy. In this embodiment, the system is configured such that the electro-magnetic field emanates from the electrode in a substantially radial pattern.

In a preferred embodiment, the source of electrical energy is an electrical signal generator that preferably operates to generate an electrical signal having a frequency between about 1 Hz to 3000 Hz, a pulse duration of between about 10-1000 us, and an amplitude of between about 1-20 volts. The electrical signal may be one or more of: a full or partial sinusoid, a square wave, a rectangular wave, and triangle wave. By way of example, the at least one electrical signal may be of a frequency between about 15 Hz to 35 Hz. Alternatively, the at least one electrical signal may be of a frequency of about 25 Hz. By way of example, the at least one electrical signal may have a pulsed on-time of between about 50 to 1000 microseconds, such as between about 100 to 300 microseconds, or about 200 microseconds. By way of example, the at least one electrical signal may have an amplitude of about 5-15 volts, such as about 12 volts.

In a method according to the present invention, a target tissue on or in a patient is contacted with an electrically-permeable or ion-permeable section of an enclosure. Conductive fluid is delivered within the interior of the enclosure and electrical energy is applied to the conductive fluid such that the electrical energy passes through the ion-permeable section of the enclosure to the target tissue. In one embodiment, the electrical energy is applied to an electrode positioned within the enclosure and surrounded by the conductive fluid. In an alternative embodiment, the electrical energy is applied directly to the conductive fluid.

In accordance with one or more preferred embodiments of the present invention, devices and methods for the treatment of one or more ailments may include: a nasogastral (NG) tube having an internal passageway and an external surface; at least one electrode coupled to the external surface of the NG tube; a conductor extending through the internal passageway of the NG tube and electrically connecting to the electrode; and a balloon surrounding the electrode and a portion of the NG tube such that when the balloon is inflated with fluid, the electrode is substantially centrally located within an interior volume of the balloon.

The device may further include an electrical signal generator operating to apply at least one electrical signal to the conductor such that, when the inflated balloon and electrode combination is positioned in an esophagus of a mammal, an electromagnetic field emanates from the electrode to the anatomy of the mammal, such as to the vagus nerve. In this embodiment, the balloon is preferably sized and shaped such that it operates to: (i) slide, in a deflated state, past a cricoid cartilage of the mammal, and (ii) seat, when in an inflated state, when slid back toward the cricoid cartilage. In accordance with one embodiment, the electrical signal, in combination with the electrical characteristics of the electrode, the fluid, and the material of the balloon, are adapted to modulate, stimulate, inhibit or block electrical signals in parasympathetic nerves, such as the vagus nerve, and/or sympathetic nerves to reduce the magnitude of constriction of bronchial smooth muscle of the mammal that may be associated with asthma, COPD, anaphylaxis or other airway disorders. In other embodiments, the electrical signal is adapted to reduce, stimulate, inhibit or block electrical signals in nerves, such as the vagus nerve, sympathetic nerves or the spinal cord, to either reduce or increase a blood pressure of the mammal or to treat other ailments, such as orthostatic hypotension, hypotension associated with sepsis or anaphylaxis, post-operative ileus, hypertension, asthma, COPD, sepsis, epilepsy, depression, obesity and any other ailment affected by nerve transmissions.

Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise arrangements and instrumentalities shown.

FIG. 1A is a schematic view of an esophageal electrode device in accordance with one or more aspects of the present invention;

FIG. 1B is a cross-sectional view taken through the balloon of the esophageal electrode device of FIG. 1A;

DETAILED DESCRIPTION OF THE PREFERRED EMBODIMENTS

Figure 2A:
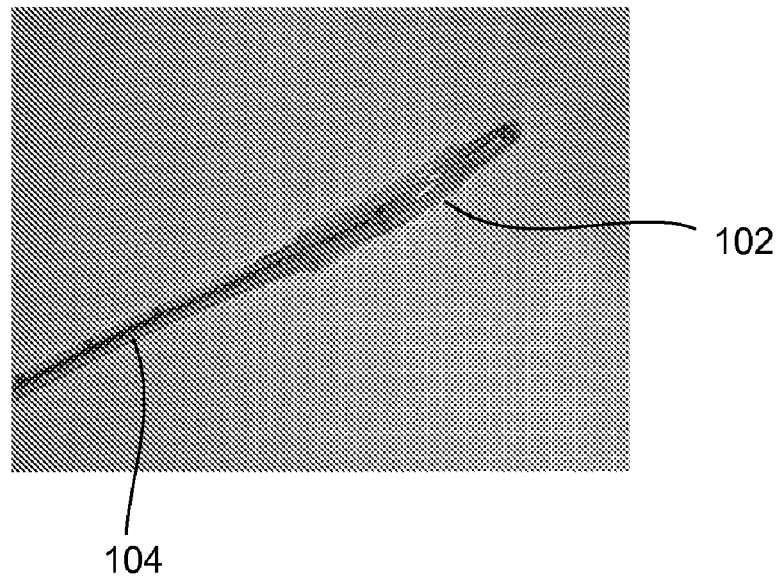
FIG. 2A is an illustration of a deflated balloon of the esophageal electrode device of FIG. 1A.

In the present invention, electrical energy is applied to one or more electrodes in the presence of an electrically conductive fluid to deliver an electromagnetic field to a patient. The techniques of the present invention may be performed in a conventional open surgery environment or in a minimally invasive manner through a natural body orifice, percutaneously through the patient's skin or using cannulas or port access devices. The invention is particularly useful for applying electrical impulses that interact with the signals of one or more nerves, or muscles, to achieve a therapeutic result, such as relaxation of the smooth muscle of the bronchia, increase in blood pressure associated with orthostatic hypotension, reduction in blood pressure, treatment of epilepsy, treating ileus conditions, depression, anaphylaxis, obesity, and/or any other ailment affected by nerve transmissions, such as the vagus nerve or the spinal cord. In particular, the present invention can be used to practice the treatments described in the following commonly assigned patent applications: US Patent Publication Numbers: 2009/0183237, 2008/0009913, 2007/0191902, 2007/0191905, 2007/0106339, 2007/0106338 and 2007/0106337, the full disclosures of which are incorporated herein by reference.

For convenience, the remaining disclosure will be directed specifically to the treatment of the vagus nerve with a device introduced through the esophagus or the trachea of a patient, but it will be appreciated that the systems and methods of the present invention can be applied equally well to other tissues and nerves of the body, including but not limited to other parasympathetic nerves, sympathetic nerves, spinal or cranial nerves, e.g., optic nerve, facial nerves, vestibulocochlear nerves and the like. In addition, the present invention can be applied to treat other ailments, such as asthma, COPD, sepsis, dialytic hypotension, epilepsy, depression or obesity and other procedures including open procedures, intravascular procedures, interventional cardiology procedures, urology, laparoscopy, general surgery, arthroscopy, thoracoscopy or other cardiac procedures, cosmetic surgery, orthopedics, gynecology, otorhinolaryngology, spinal and neurologic procedures, oncology procedures and the like.

With reference to FIGS. 1A, 1B, an exemplary device 100 for delivering an electromagnetic field to a patient will now be described. Device 100 is designed to be introduced into the esophagus of the patient and located therein at a position that (when activated) achieves a therapeutic result. The device 100 includes an inflatable balloon 102 and a catheter, or nasogastral (NG) tube 104, sized and shaped (when the balloon 102 is deflated) to slide into the patient's esophagus.

The balloon 102 has at least one section formed from an electrically-permeable material, preferably a hydrophilic or ion-permeable material. By way of example, balloon 102 may be substantially formed from an ion-permeable, soft, flexible, and/or distensible material with a thickness of about 0.001 inches. Suitable balloon materials for use in the present invention include Pebax®, aromatic polyether polyurethane grades, such as Dureflex® from, for example, Deerfield Urethane in Whately, Mass., thermally conductive polymers or thermoplastic elastomers (TPE) such as those found at Cool Polymers, Inc. in Warwick, R.I. and the like. However, it will be recognized by those skilled in the art that a variety of commercially available balloon materials may be used to carry out the present invention.

The balloon preferably has a length of between about 1-3 cm (such as 2 cm), a diameter of between about 1.5-4.0 cm (such as 2-3 cm), and a fluid pressure therein of between about 1-10 pounds per square inch (such as 2 psi) when inflated. Obviously, under the stresses experienced during insertion, extraction and inflation, the balloon 102 should not separate from the NG tube 104, tear or leak. The NG tube 104 may be of a standard type formed out of polyurethane, measuring about 36 cm long, and having inside and outside diameters of 1.6 mm and 2.5 mm, respectively (although other lengths, diameters, and materials may be employed). In order to assist in the placement of the balloon 102 at a desired location within the esophagus, the NG tube 104 may include markers along its length, such as one marker about every 1 cm.

With reference to FIG. 1B, the NG tube 104 includes an internal passageway 106 and an external surface 108. At least one electrode 110 is coupled to the external surface 108 of the NG tube 104 (such as by a UV curable adhesive, such as Dymax 204-CTH). By way of example, the at least one electrode 110 may be of a general cylindrical shape and may extend around the external surface 108 of the NG tube 104. Although there are a number of sizes and shapes that would suffice to implement the electrode 110, by way of example, the at least one electrode 110 may be between about 1.0-1.5 mm long (such as 1.27 mm), may have an outside diameter of between about 2.6-2.85 mm (such as 2.77 mm), and may have an inside diameter of between about 2.5-2.75 mm (such as 2.67 mm). A suitable electrode 110 may be formed from Pt-IR (90%/10%), although other materials or combinations or materials may be used, such as platinum, tungsten, gold, copper, palladium, silver or the like.

Those skilled in the art will also recognize that a variety of different shapes and sizes of electrodes may be used. By way of example only, electrode shapes according to the present invention can include ball shapes, twizzle shapes, spring shapes, twisted metal shapes, annular, solid tube shapes or the like. Alternatively, the electrode(s) may comprise a plurality of filaments, rigid or flexible brush electrode(s), coiled electrode(s) or the like. Alternatively, the electrode may be formed by the use of formed wire (e.g., by drawing round wire through a shaping die) to form electrodes with a variety of cross-sectional shapes, such as square, rectangular, L or V shaped, or the like. Alternatively, the electrode may comprise a breakaway electrode on the end of a small gauge needle (e.g., 22 GA). In this embodiment, the electrode is hollow to allow for aspiration through the needle while being inserted ensuring that no blood vessels are compromised. Once in place, the needle is withdrawn over a fine conducting wire which is attached to the electrode, leaving just the electrode near the vagus nerve. The wire is then connected to the negative terminal of source of electrical energy. In yet another embodiment, the syringe itself is the electrode. The needle is coated with a thin insulating material leaving only 1-2 mm of the distal end of the needle bare, which acts as the electrode. Since the bronchodilation effect is almost instantaneous, the needle may only need to be left in place for a short time during which bronchodilator drugs will have access to the airways.

A conductor 112 extends through the internal passageway 106 of the NG tube 104 and electrically connects to the electrode 110. By way of example, the conductor 112 may be a solid silver wire of about 0.25 mm diameter insulated with a PTFE material of about 0.33 mm diameter. The diameter of the insulating material of the conductor 112 should be less than the internal diameter of the NG tube 104 such that fluid may freely flow therein despite the presence of the conductor 112. The conductor 112 may be laser welded to the electrode 110 using known procedures.

Figure 2B:
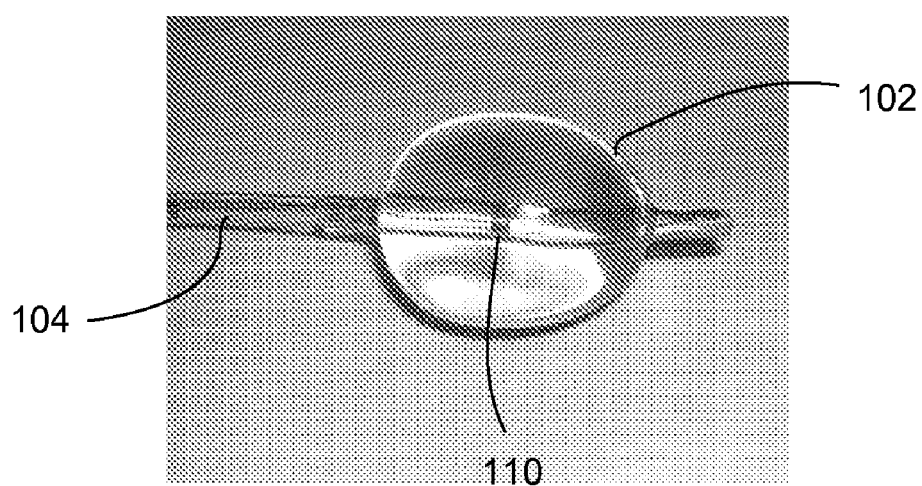
FIG. 2B is an illustration of an inflated balloon of the esophageal electrode device of FIG. 2A.

FIG. 1B is a schematic illustration of the balloon 102 in an inflated state, while FIG. 2B is a reproduction of a photograph illustrating a prototype of the device 100 with the balloon 102 inflated. FIG. 2A is a reproduction of a photograph illustrating the prototype of the device 100 with the balloon 102 deflated. A fluid, preferably a saline solution, passes into the balloon 102 through the NG tube 104 to inflate same. The balloon 102 is sized, shaped and located about the electrode 110 and a portion of the NG tube 104 such that when the balloon is inflated with fluid, the electrode 110 is substantially centrally located within an interior volume of the balloon 102. This configuration has several advantages over conventional electrode configurations, such as: (i) the metal of the electrode 110 is not too close to, and never comes in contact with, the patient's tissue, which means that there is no concern about tissue necrosis or excessive electric fields in the tissue; (ii) the electrode 110 may be used with direct current signal sources since any Faradic Products (e.g. OH$^-$, H$_2$O$_2$) would not reach excessively high concentrations at the tissue site; (iii) as the balloon 102 is filled with saline, the surface of the balloon 102 wets and permits good contact with the surrounding tissue of the patient, which may otherwise be dry; and (iv) the material of the balloon 102 is preferably very soft and flexible such that it gently conforms to the surrounding tissue of the esophagus.

To inflate the balloon 102, a number of features are provided with the device 100. A pilot balloon assembly 130, which may be of a standard type, is located at a proximal end of the device 100. The pilot balloon assembly 130 is in fluid communication with the NG tube 104 via fluid tube 132. The fluid tube 132 may enter the NG tube 104 along with the conductor 112, and the entry point may be sealed with an adhesive, such as Dymax 204-CTH UV curable adhesive. The pilot balloon assembly 130 includes a spring loaded valve that opens when introducing fluid into the pilot and the fluid tube 132, and/or when removing fluid therefrom.

The NG tube 104 may include a first aperture 114 through which the conductor 112 passes from the internal passageway 106 to the at least one electrode 110. The NG tube 104 may include second and third apertures 116, 118 extending from the internal passageway 106 to the external surface 108, and through which fluid may pass to inflate and deflate the balloon 102 (as will be discussed in more detail later herein). Preferably, the second and third apertures 116, 118 are disposed at proximal and distal ends 120, 122 of the balloon 102, respectively, and the first aperture 114 is located between the second and third apertures 116, 118.

The inflation process preferably includes a priming phase followed by an inflation phase. The priming phase preferably takes place prior to introducing the device 100 into the patient's esophagus. In the priming phase, a source of fluid, such as saline, is coupled to the pilot balloon assembly 130. The source of fluid may be a fluid filled syringe or the like. With the balloon 102 in a generally vertical orientation (with distal end 120 up), fluid is preferably introduced into the pilot, the fluid tube 132, the NG tube 104 and the balloon 102 via the syringe. The fluid will enter the balloon 102 mostly via the second and third apertures 116, 118. Air will tend to collect at the distal end 120 of the balloon 102 as the fluid enters the device and urges the air in that direction. Again, keeping the balloon upright, at least some of the fluid is drawn out of the balloon 102 by reversing the fluid flow at the pilot balloon assembly 130 and source of fluid. This reversal of fluid flow will create a vacuum and draw all the air out of the balloon 102 via the second aperture 116. Of course, there may be other ways to prime the device 100, however, the above approach is believed to be suitable.

After the device 100 is inserted into the patient's esophagus (preferably through the nasal passage), the inflation phase begins. The inflation phase includes causing the fluid to flow into the device 100 from the source (e.g., the syringe) until a desired balloon size and/or pressure is reached, such as the aforementioned 1-3 cm length, 1.5-4.0 cm diameter, and/or 1-10 psi pressure.

The electrical properties of the electrode 110, the fluid, and the material of the balloon 102 are preferably designed such that a resistance therethrough is no more than about 1000 Ohms, preferably no more than 500 Ohms and more preferably 200 Ohms or less. In an exemplary embodiment, the impedance through the electrode 110, the fluid, and the material of the balloon 102 should be no more than about 200 Ohms at 1000 Hz. The electrical properties of the fluid may be as important as those of the electrode 110 in this regard. The electrically conducting fluid should have a threshold conductivity to provide a suitable conductive path between electrode 110 and the outer wall of the balloon 102. The electrical conductivity of the fluid (in units of milliSiemans per centimeter or mS/cm) will typically be between about 1 mS/cm and 200 mS/cm and will usually be greater than 10 mS/cm, preferably will be greater than 20 mS/cm and more preferably greater than 50 mS/cm. In one embodiment, the electrically conductive fluid is isotonic saline, which has a conductivity of about 17 mS/cm. Applicant has found that a more conductive fluid, or one with a higher ionic concentration, will usually provide optimal results. For example, a saline solution with higher levels of sodium chloride than conventional saline (which is on the order of about 0.9% sodium chloride) e.g., on the order of greater than 1% or between about 3% and 20%, may be desirable. A fluid of about 5% saline (e.g., approximately 100 mS/cm) is believed to work well, although modifications to the concentration and the chemical make-up of the fluid may be determined through simple experimentation by skilled artisans.

As noted above, the material of the balloon 102 is preferably slightly water-permeable or hydrophilic so that when the balloon 102 is filled with saline, the surface of the balloon 102 wets. Preferably, when filled with 10 cc of saline, the flux of saline out of the balloon 102 (into a similar saline solution) should not exceed about 1 cc per hour. Lubrizol Tecophilic HP93A-100 is a material with these properties.

In an alternative embodiment, the electrode 110 may be implemented via the fluid itself within the balloon 102. Although a 5% saline solution would have a relatively high resistance compared to a metal electrode 110 implementation, those skilled in the art would appreciate that higher conductivity fluid solutions may be employed for such purposes or a larger diameter and/or shorter tube may be utilized to increase the conductivity. Additionally or alternatively, the conductor 112 may be implemented using the conductive fluid used to fill the balloon 102; indeed, such fluid is within the passage 106 anyway. Again, relatively high conductivity fluid would be desirable.

Figure 3:
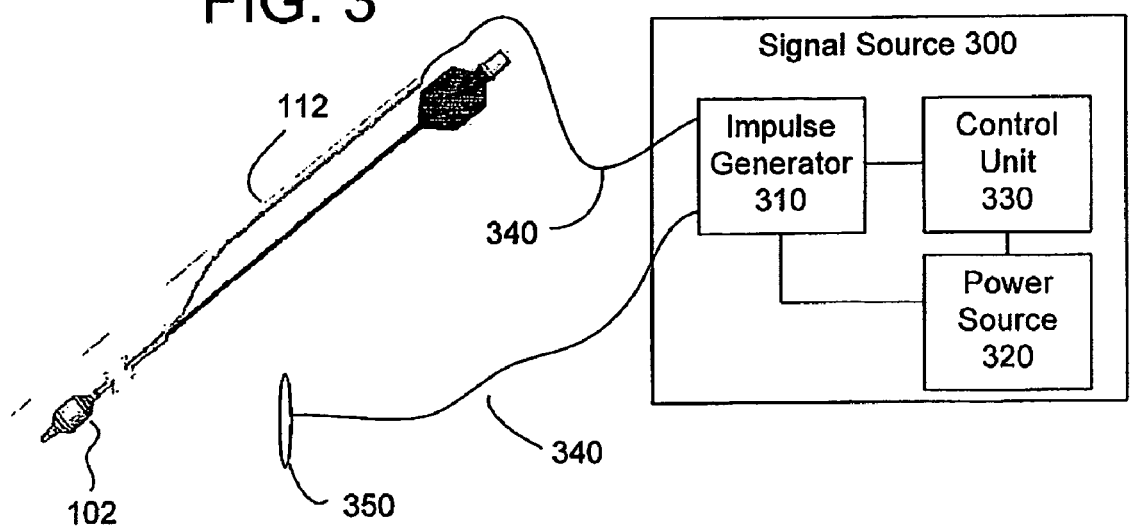
FIG. 3 is a schematic diagram of an electrical signal generating system for use with the esophageal electrode device of FIG. 1A.

With reference to FIG. 3, a complete system for using the device 100 includes an electrical signal generator (or source) 300. Source 300 operates to apply at least one electrical signal to the conductor 112 (via lead 340) such that, when the inflated balloon 102 (and electrode 110) is positioned in the esophagus of a patient, an electromagnetic field emanates from the electrode 110 to the anatomy of the mammal in the vicinity of the esophagus to achieve a therapeutic result. Unlike some known techniques, which target a specific location of the patient's anatomy, such as a very specific location of a nerve, the return electrode 350 placement is preferably such that when applied to the mammal, the electromagnetic field emanating from the electrode 110 is a substantially radial pattern—in other words, the pattern of the electromagnetic field emanating from the electrode 110 is not focused on any particular point, or small, localized region of the patient's anatomy. This is preferably achieved by applying the return electrode 350 to an external portion of the patient, such as to at least one of the upper-back, the chest, and/or the stomach.

The source 300 may be tailored for the treatment of a particular ailment and may include an electrical impulse generator 310, a power source 320 coupled to the electrical impulse generator 310, and a control unit 330 in communication with the electrical impulse generator 310 and the power source 320. Electrodes 340 provide source and return paths for the at least one electrical signal to/from the electrode 110 and return electrode 350.

The control unit 330 may control the electrical impulse generator 310 for generation of the signal suitable for amelioration of the ailment when the signal is applied via the electrodes 340 to the device 100. It is noted that source 300 may be referred to by its function as a pulse generator.

Figure 4:
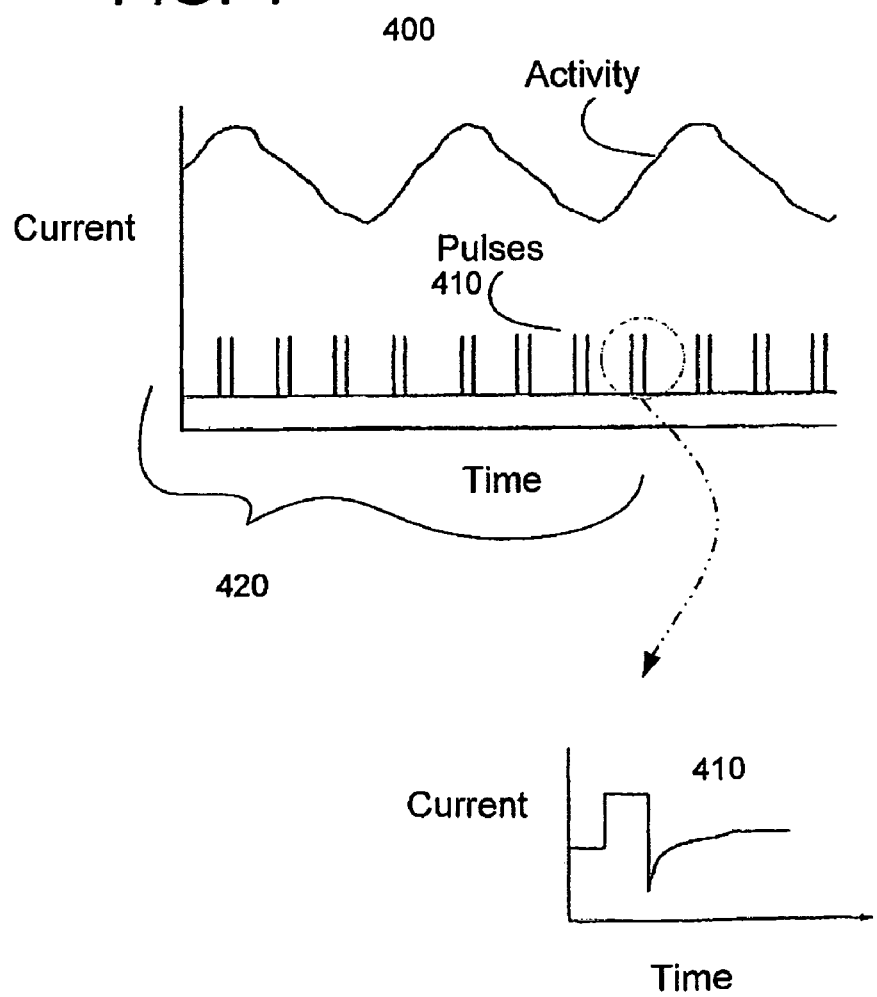
FIG. 4 illustrates an exemplary electrical voltage-current profile for a blocking and/or modulating impulse in accordance with an embodiment of the present invention.

FIG. 4 illustrates an exemplary electrical voltage/current profile for a stimulating, blocking and/or modulating impulse applied to a portion or portions of the patient's anatomy, in accordance with one or more embodiments of the present invention. A suitable electrical voltage/current profile 400 for the stimulating, blocking and/or modulating impulse 410 to the portion or portions of one or more nerves and/or muscles may be achieved using the pulse generator 310. In a preferred embodiment, the pulse generator 310 may be implemented using the power source 320 and control unit 330 having, for instance, a processor, a clock, a memory, etc., to produce a pulse train 420 to the electrode(s) 340 that deliver the blocking and/or modulating fields to the nerve resulting from impulses 410.

The parameters of the modulation signal 400 are preferably programmable, such as the frequency, amplitude, duty cycle, pulse width, pulse shape, etc. The blocking and/or modulating impulse signal 410 preferably has a frequency, an amplitude, a duty cycle, a pulse width, a pulse shape, etc. selected to influence the therapeutic result, such as stimulating, blocking and/or modulating some or all of one or more nerve transmissions.

While the exact physiological causes of, for example, asthma and anaphylaxis have not been determined, the present invention postulates that the direct mediation of the smooth muscle constriction of the bronchia is the result of activity in the vagus nerve. Specifically, one or more embodiments of the present invention consider the signals carried by the vagus (parasympathetic) nerve to cause a constriction of the smooth muscle surrounding the bronchial passages. Certain signals of the parasympathetic nerve fibers carry the opposing signals that tend to open the bronchial passages (it is believed that there are no direct sympathetic innervations of the bronchial smooth muscle, although the sympathetic nerves may have an indirect effect on the bronchial smooth muscle). Specifically, it should be recognized that certain signals, such as the cholinergic fibers of the vagus nerve mediate a response similar to that of histamine, while other signals of the vagus nerve (e.g., nonadrenergic, noncholinergic or NANC nerve fibers) generate an effect similar to epinephrine. Given the postulated balance between these signals, stimulating the NANC nerve fibers and/or blocking or removing the cholinergic signals should create an imbalance emphasizing the NANC signal. Along these lines, scientific literature also indicates that severing the vagus nerve in dogs will open the bronchial passages, much the same way that epinephrine does.

In accordance with at least one aspect of the present invention, the delivery of an electromagnetic field sufficient to stimulate, block and/or modulate transmission of signals in the vagus nerve will result in relaxation of the bronchi smooth muscle, dilating airways and/or counteracting the effect of histamine on the vagus nerve. Depending on the placement of the field, the stimulating, blocking and/or modulating signal can also raise the heart function.

For example, assuming the aforementioned impedance characteristics of the device 100, the at least one electrical signal may be of a frequency between about 1 Hz to 3000 Hz, a pulse duration of between about 10-1000 us, and an amplitude of between about 1-20 volts. For example, the at least one electrical signal may be of a frequency between about 15 Hz to 35 Hz, such as about 25 Hz. The at least one electrical signal may have a pulsed on-time of between about 50 to 1000 microseconds, such as between about 100 to 300 microseconds, such as about 200 microseconds. The at least one electrical signal may have an amplitude of about 5-15 volts, such as about 12 volts. The at least one electrical signal may include one or more of a full or partial sinusoid, a square wave, a rectangular wave, and triangle wave.

Although the specific implementation of the signal source 300 is not of criticality to the invention, by way of example, the source 300 may be purchased commercially, such as a Model 7432 available from Medtronic, Inc.

Alternatively, U.S. Patent Application Publications 2005/0075701 and 2005/0075702, both to Shafer, both of which are incorporated herein by reference, contain descriptions of pulse generators that may be applicable for implementing the signal source 300 of the present invention.

An alternative implementation for the signal source 300 of the present invention may be obtained from the disclosure of U.S. Patent Publication No.: 2005/0216062, the entire disclosure of which is incorporated herein by reference. U.S. Patent Publication No.: 2005/0216062 discloses a multi-functional electrical stimulation (ES) system adapted to yield output signals for effecting faradic, electromagnetic or other forms of electrical stimulation for a broad spectrum of different biological and biomedical applications. The system includes an ES signal stage having a selector coupled to a plurality of different signal generators, each producing a signal having a distinct shape such as a sine, a square or saw-tooth wave, or simple or complex pulse, the parameters of which are adjustable in regard to amplitude, duration, repetition rate and other variables. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated.

A general approach to treating an ailment, such as bronchial constriction, hypotension, epilepsy, depression, obesity, and any other ailment affected by vagus nerve transmissions, etc., in accordance with one or more embodiments of the invention may include a method of (or apparatus for) treatment, comprising: inserting the balloon-electrode device 100 into an esophagus of the patient; inflating the balloon with fluid such that the electrode is substantially centrally located within an interior volume of the balloon; and applying at least one electrical signal to the electrode via the conductor such that an electromagnetic field emanates from the electrode to at least one nerve and/or muscle of the patient in the vicinity of the esophagus of the patient. The at least one electrical signal, in combination with electrical characteristics of the electrode, the fluid, and the material of the balloon, are such that at least one of: (i) a magnitude of constriction of bronchial smooth muscle of the mammal is reduced, (ii) the blood pressure of the mammal is either reduced or increased, (iii) incidents/magnitude of epilepsy episodes are reduced, (iv) depression is reduced, (v) obesity is reduced, (vi) post-operative ileus is resolved; and (vi) any other ailment affected by vagus nerve transmissions is improved.

The step of inserting the balloon-electrode device 100 and inflating the balloon 102 may include: inserting the balloon-electrode device 100 in a deflated state (but preferably primed) past a cricoid cartilage of the patient, inflating the balloon 102, and extracting the balloon 102 back toward the cricoid cartilage until it seats. Other approaches to positioning the balloon 102 may be used, such as using the hash marks discussed above.

Again, assuming the aforementioned impedance characteristics of the device 100, the at least one electrical signal may be of a frequency between about 1 Hz to 3000 Hz, a pulse duration of between about 10-1000 us, and an amplitude of between about 1-20 volts. The polarity of the pulses may be maintained either positive or negative. Alternatively, the polarity of the pulses may be positive for some periods of the wave and negative for some other periods of the wave. By way of example, the polarity of the pulses may be altered from time to time or periodically.

Experiments were performed to identify exemplary methods of how the electromagnetic fields may be supplied to the patient to (i) reduce the sensitivity of the bronchial smooth muscle to the nerve signals to constrict, (ii) to blunt the intensity of, or break the constriction once it has been initiated.

Experimental pigs were pretreated with an intramuscular injection of 4.4 mg/kg Telazol and 2.2 mg/kg Xylazine, had venous access established in both ears for drug delivery, were intubated, and anesthetized with 1.5-3% isoflurane. The animals were maintained at 37° C. using a homeothermic heating pad placed on a ventilator (13-14 stroke/minute, 250-350 ml tidal volume, 35-45 mmHg $CO_2$, using Siemens equipment). A cannula was inserted into the left carotid artery to monitor blood pressure. After cannula insertion, the anesthesia was modified to use alpha chloralose (1 g/kg bolus and 1.5 g/hr infusion) and 0.3% isoflurane inhalation. The animals were ventilated through an endotracheal tube to provide positive pressure and constant volume ventilation. Pulmonary inflation pressure (ppi) and blood pressure were recorded and stored digitally (using pressure transducers and software by Biopac Systems Inc., Goleta, Calif.).

A balloon-electrode device 100 was inserted into the esophagus of the animals and positioned proximate to the nerves of interest (e.g., the vagus nerve). A conducting saline solution (5% NaCl) was introduced into the expanding balloon. The balloon was filled until it made contact with the inner wall of the esophagus (approximately a 1 cm radius). The wire attached to the electrode was then connected to a signal generator which delivered a square wave voltage pulse of 200 us duration, repeated at 25 Hz at voltages from 1 to 12 volts. The electrocaudery grounding plate, on the animal's back, or an EKG electrode placed on the animal's stomach, was used as the return electrode.

Figure 5A:
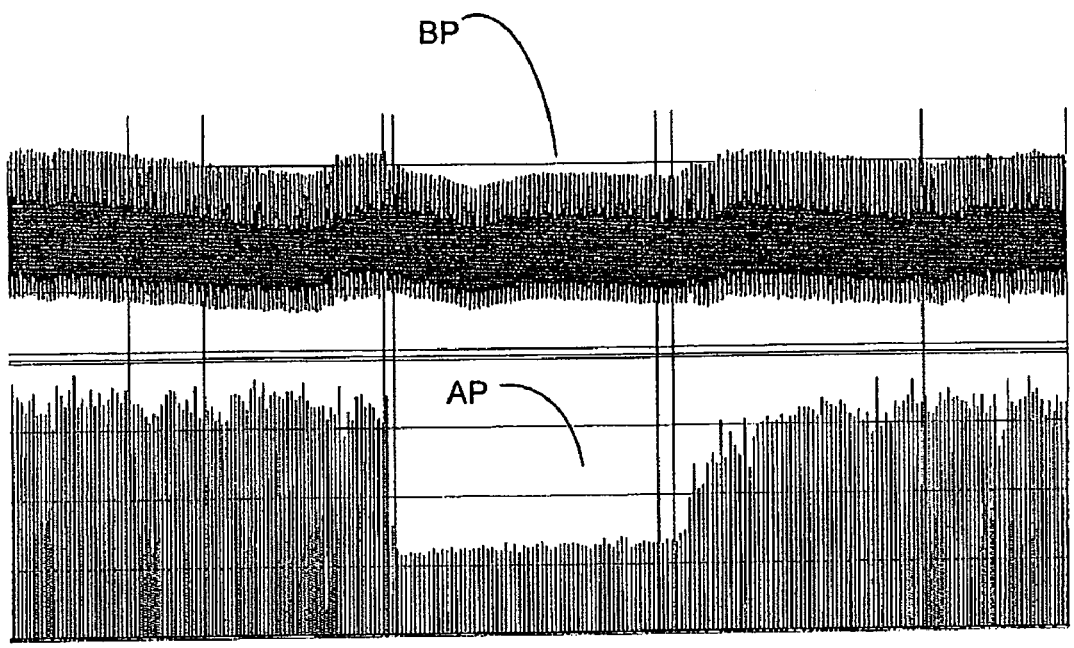
FIGS. 5A, 5B, 5C graphically illustrate exemplary experimental data obtained in accordance with multiple embodiments of the present invention.
Figure 5B:
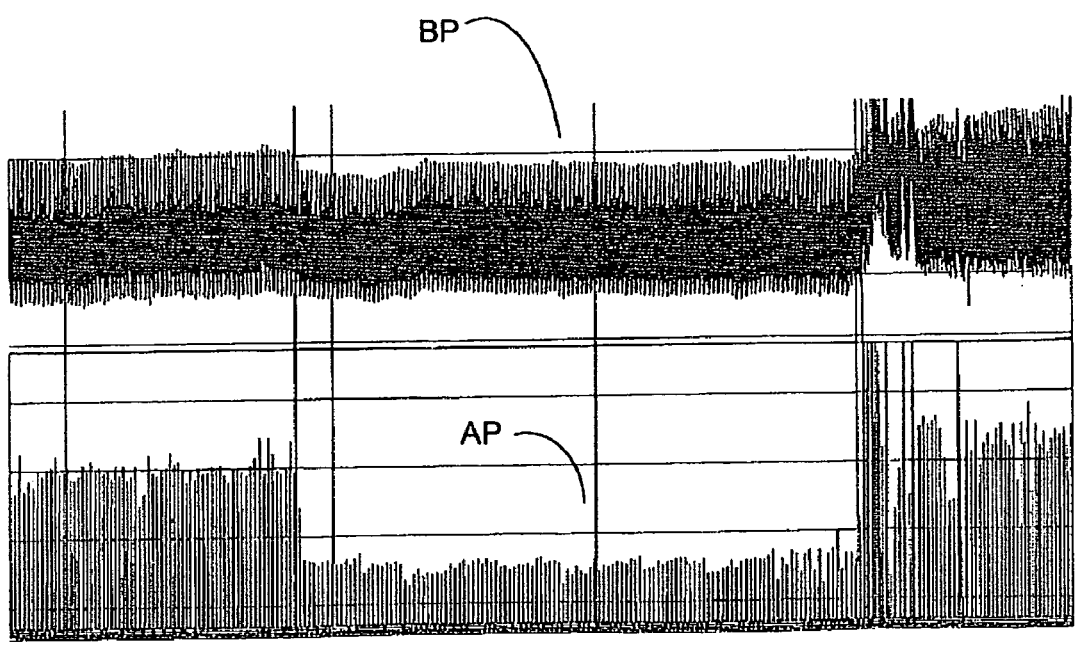
Figure 5C:
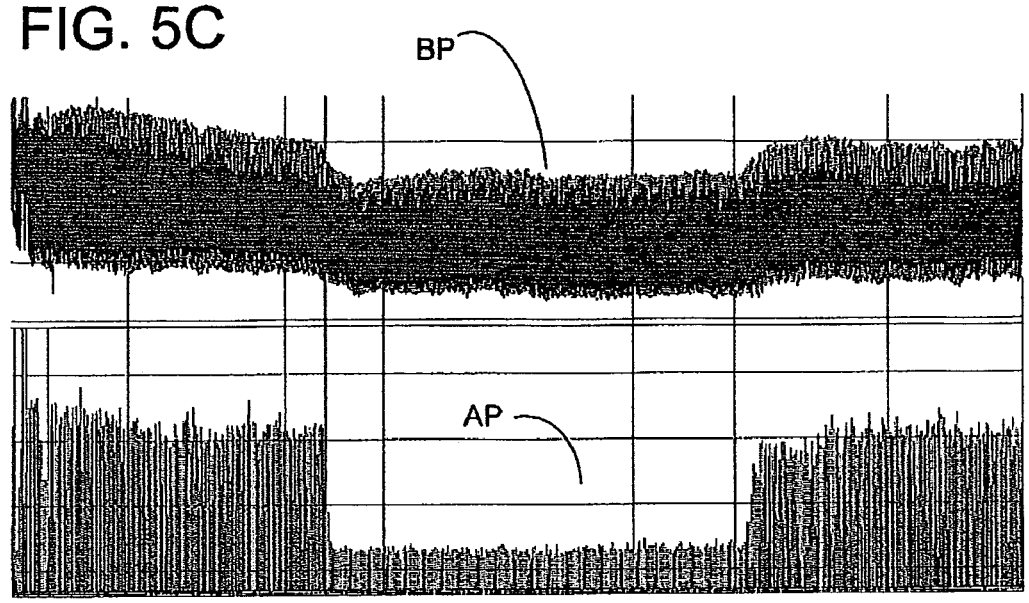

As shown in FIGS. 5A, 5B and 5C, electrical stimulation from within the esophagus caused rapid and significant drops in baseline airway resistance, along with corresponding drops in blood pressure. In all the graphs, the top line BP shows blood pressure, and the second line AP shows airway pressure. The electrical stimulation was maintained for up to 30 minutes (the maximum stimulation duration).

The esophageal electrode device 100 was also tested on twelve human patients to determine the safety of the procedure, ease of insertion, patient acceptability and effects of electrical stimulation. In one patient, the esophageal electrode was inserted in one nostril and monitored continuously during insertion with a bronchoscope in the other nostril. No anesthesia was applied to the back of the throat but a standard lidocaine lubricant was placed on the ends of both the scope and the esophageal electrode before insertion. Insertion of the esophageal electrode through the nose and in to the throat took only a few seconds and was painless. When it reached the back of the throat, the patient was instructed to swallow repeatedly while the electrode was fed down the esophagus. There was a little irritation until the electrode was swallowed and then it was fairly comfortable. Next, about 6 cc of a room temperature 5% saline solution was injected in to the balloon. A cool sensation was felt in the throat but there was little discomfort and no gag reflex. The expanded balloon remained for several minutes. Swallowing was not hindered.

Blood pressure measurements were taken every few minutes with an automatic blood pressure cuff to monitor any changes in blood pressure. The generator was then turned on and voltage slowly increased. At about 8-10 volts a slight sensation was felt in the esophagus and/or under the electrosurgical grounding pad electrode (placed over the right pectoral muscle). The sensation was not unpleasant and the voltage was then turned up to its maximum, 12 V. Diastolic blood pressure increased from 90 to about 100 mm Hg during the procedure but may not have been related to the stimulation as the patient was somewhat nervous.

It was noted that when one attempted to pull the balloon up to the cricoid cartilage (the position of optimal response in the pig model), some resistance was felt. This information is believed to indicate a simple and precise positioning process: insert the balloon past the cricoid cartilage, inflate it, and then pull it back until it "seats" in the correct position.

To remove the electrode, fluid was sucked out of the balloon and the electrode was simply pulled from the esophagus and out through the nose. This process was painless and took just a few seconds.

A second balloon was inserted and the whole process repeated with similar results. Blood pressure remained elevated and did not increase with the second stimulation relative to its pre-stimulation level. Eleven other patients have been treated this way with similar results.

Figure 6:
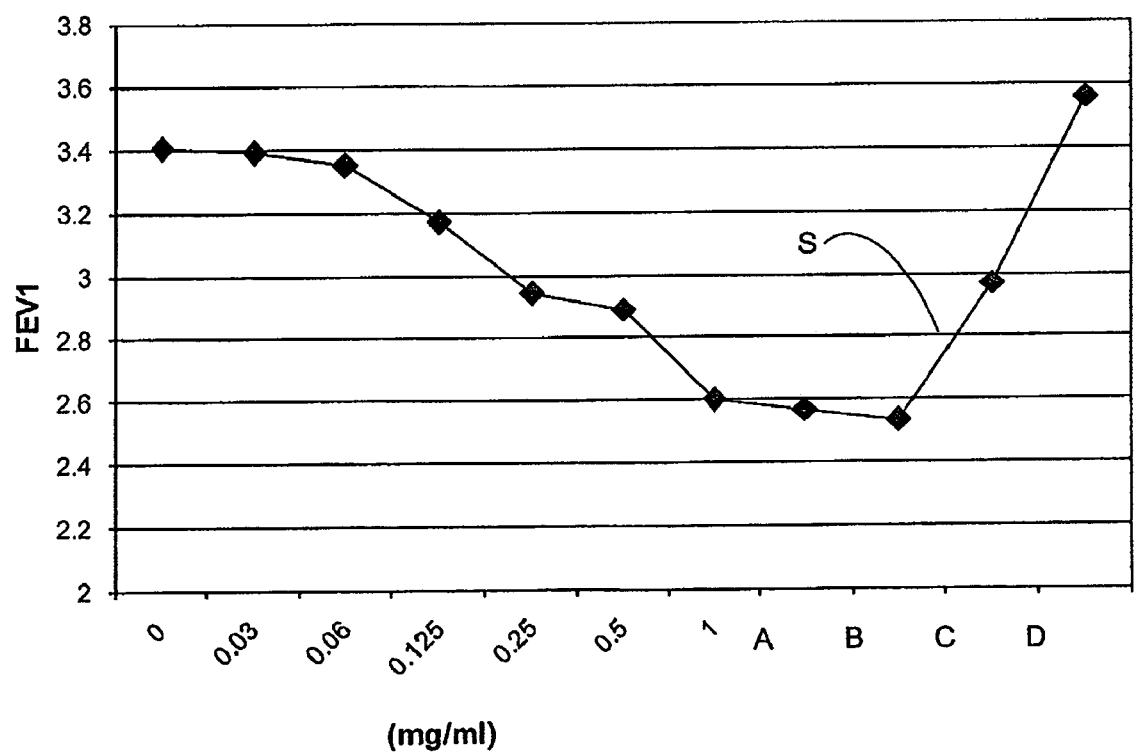
FIG. 6 graphically illustrates further experimental data obtained in accordance with embodiments of the present invention.

With reference to FIG. 6, in a further experiment on a human, increasing doses of methacholine were given to a patient until a drop of about 24% in forced expiratory volume (FEV) was observed at 1 mg/ml. (In the context of this application, forced expiratory volume is a measure of the maximum amount of air during a forced vital capacity determination that can be expelled in a given number of seconds. A second FEV was taken (point A on the chart) prior to introducing the esophageal electrode device 100. The esophageal electrode device 100 was then inserted and another FEV was taken (point B). The stimulator was then turned on over interval S (from point C-D) to provide a signal having parameters consistent with those above, particularly with an amplitude of about 10 V for 4 minutes. The esophageal electrode device 100 was then removed and a post stimulation FEV was taken at point D, which shows a 16% increase. A final rescue albuterol treatment (post point D) restored the patient to normal FEV.

Figure 7A:
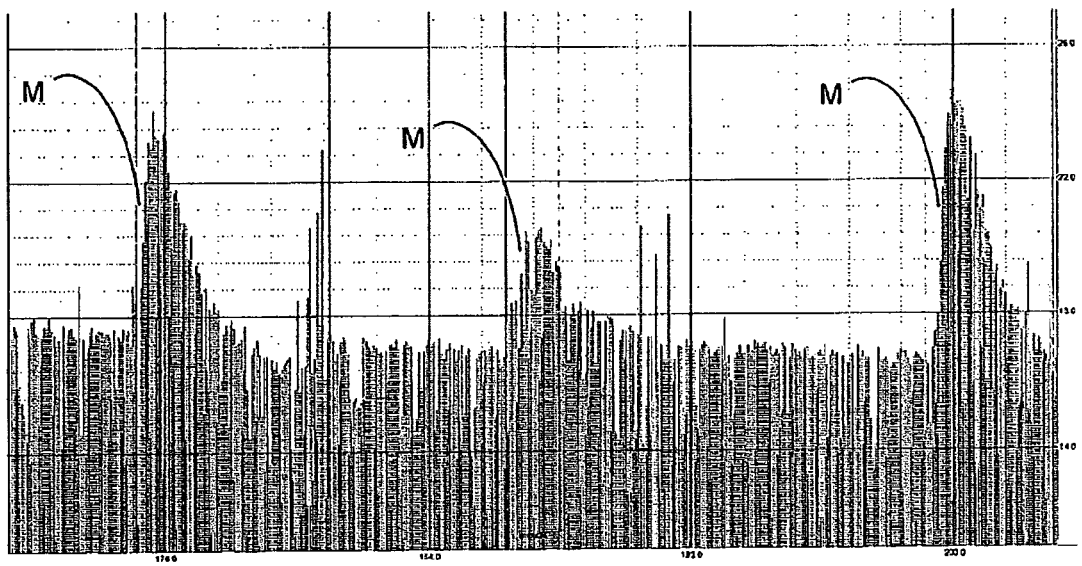
FIGS. 7A-7B graphically illustrate still further experimental data obtained in accordance with the present invention.
Figure 7B:
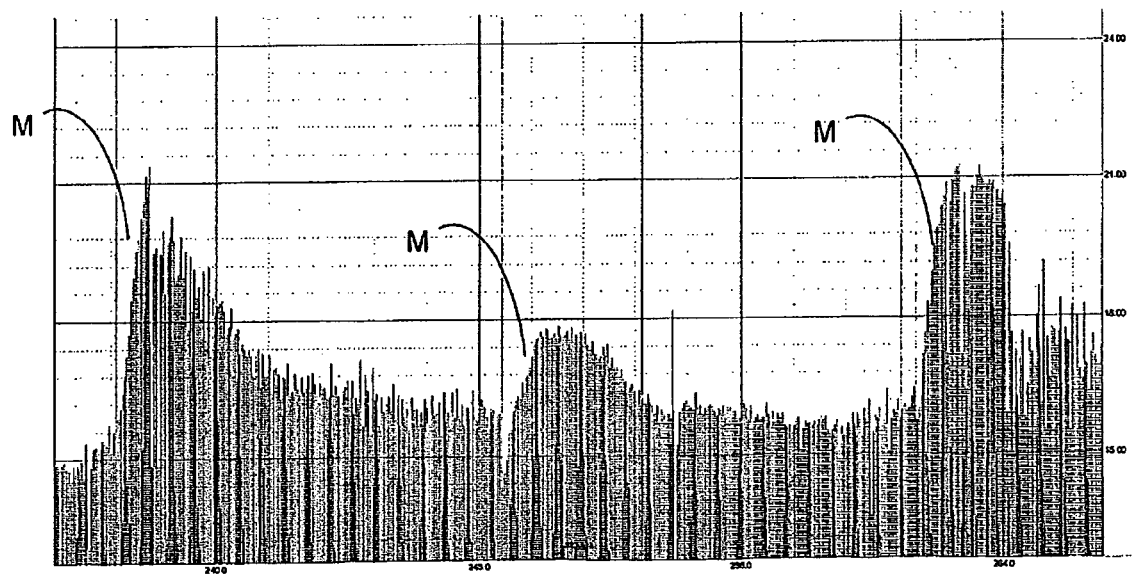

With reference to FIGS. 7A-7B, further experiments were conducted on pigs. In each of FIGS. 7A and 7B, airway pressure changes were measured in response to three methacholine challenges by nebulizer (indicated by the labels M). Each methacholine challenge was followed by an electrical stimulation through an esophageal electrode device 100 using signal parameters consistent with those discussed above. Two control traces bracket each challenge and stimulation. In the middle trace of each figure, electrical stimulation was applied just prior to turning on the nebulizer and remained on until just after the airway pressure peak. The stimulation using the esophageal electrode device 100 reduced the peak pressure increase by about 50%.

The present invention may also be used for the treatment of infections within a patient's body. It is well known that colloidal silver is a catalyst that disables and kills certain specific enzymes, particularly those enzymes that microorganisms depend upon to breathe. Colloidal silver is often used to reduce inflammation and promote healing of injured tissues because microbes are unlikely to develop a resistance against the silver as they often do against conventional and highly targeted antibodies. This is because silver attacks a broad range of enzyme targets within the organisms. Unlike pharmaceutical antibiotics that also destroy beneficial enzymes, colloidal silver typically leaves the tissue-cell enzymes intact. In one embodiment of the invention, the outer surface of the balloon is coated with colloidal silver and the electrode is positively charged, i.e., anodic, to create positively charged silver ions that can be driven into infected tissue to treat the infection.

In one particular aspect of this embodiment, the balloon is adapted for use with fractures, particularly open fractures (i.e., wherein the bone has pushed through the skin leaving it open to the air) which have a high risk of developing infections. In a preferred embodiment, a balloon as described above is sized and shaped for placement within the medullary canal of an open tibia fracture, although it will be recognized that the invention can be used to treat a variety of different fractures. In this embodiment, the balloon has an outer surfaced coated with silver, e.g., colloidal silver. Typically, the balloon would be placed during the two or three days of cleaning and debridement prior to intramedullary rodding and final closing. Once positioned, the balloon is inflated with an electrically conductive fluid such that the balloon conforms to the bone surrounding the medullary canal. The invention is particularly useful for this application because the balloon can be formed of an elastic material that will inflate to the shape of the surrounding structure within the canal. After inflation, an electrical signal is applied to a positively-charged electrode within the balloon to transmit electrical energy through the conductive fluid and the silver-coated outer surface of the balloon, thereby driving positively charged silver ions into the tissue to treat the infection.

In another alternative embodiment, the invention may be useful as an improved spinal cord stimulator. Spinal cord stimulators are implantable devices used to treat chronic neurological pain. Typically, one or more electrodes are implanted in the epidural space either percutaneously or by surgical laminectomy or laminotomy. A pulse generator or RF receiver may be implanted, for example in the abdomen or buttocks, to apply an electric impulse to the electrode(s) to block pain signals from reaching the brain such that the patient receives a mild tingling sensation in lieu of the pain. One of the challenges with conventional spinal cord stimulators is that the electrode lead must have a small enough diameter (typically less than 3 mm and often less than 2 mm) to fit through the entry point to the patient. However, once inside the epidural space, it is desirable to contact as large an area of the dura as possible to achieve ideal stimulation. Thus, conventional electrode leads typically have multiple electrodes spaced along the shaft of the electrode lead to achieve greater contact area with the dura. In addition, the physician typically must experiment with the placement of the electrode lead in different locations on the dura in an attempt to optimize the effect. Another challenge with conventional devices is that the electrode leads tend to migrate after positioning, which can reduce the efficiency of these leads over time.

The present invention provides a system and method for introducing a spinal cord stimulation electrode device into a patient's epidural space through a small portal (i.e., on the order of less than 5 mm, preferably less than 2 mm) and then expanding the electrode device once inside the epidural space to achieve a larger footprint of contact on the dura. This mitigates migration of the electrode within the epidural space and provides for more efficient and effective treatment.

Figure 8A:
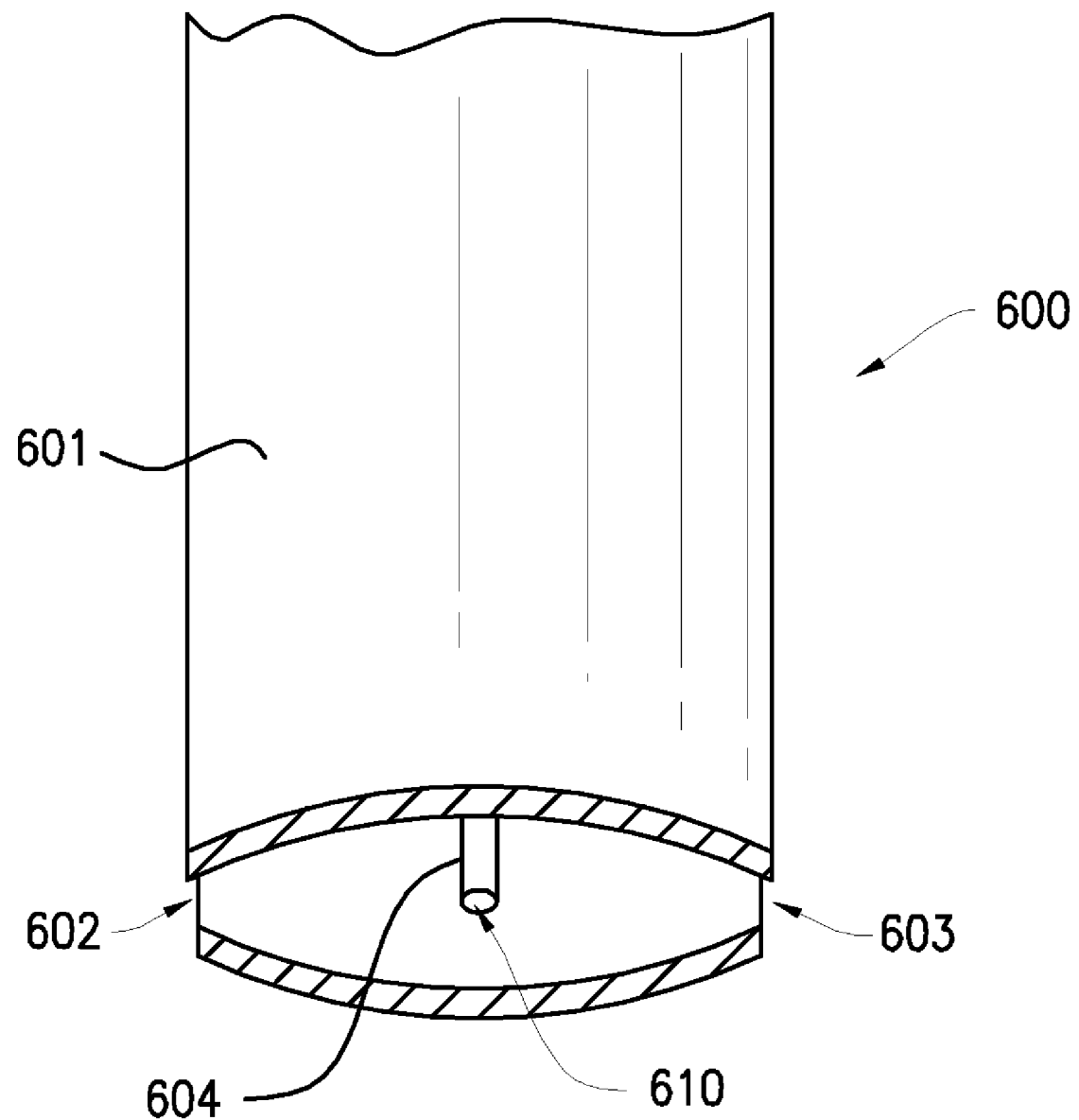
FIGS. 8A-8B illustrate another embodiment of the present invention for stimulation of the spinal cord.

FIG. 8A is a partial cross-sectional view of a distal portion of an exemplary device 600, such as an electrode lead for stimulating tissue, such as a nerve. As shown, electrode lead device 600 comprises an electrode shaft 601 provided with lateral openings 602, 603 in the distal region of shaft 601. In this embodiment, device 600 is an electrode lead coupled to a pulse generator or RF receiver (not shown) designed to apply an electric impulse to block or modulate pain signals traveling through a nerve to the patient's brain. Spinal cord stimulators are well known in the art. Examples of conventional electrode leads for such stimulators are the Restore Advanced Neurostimulator sold by Medtronic or the electrodes leads sold by AD-Tech Medical Instrument Corp. It will also be recognized that other configurations are possible. For example, device 600 may be an insulated shaft that houses one or more electrode(s) therein.

As shown, a fluid passage 604 extends through the interior of electrode shaft 601. Fluid passage 604 is coupled to a source of electrically conductive fluid (not shown). In use, device 600 is introduced into the epidural space of the patient such that the distal region of electrode shaft 601 is adjacent to or in contact with a target area within the epidural space, such as the dura. Device 600 may be introduced into the epidural space percutaneously or in a variety of manners well known in the art. Fluid passage 604 has a distal opening 610 for delivery of the electrically conductive fluid into the interior of a balloon 612 (see FIG. 8B) housed within electrode shaft 601.

Figure 8B:
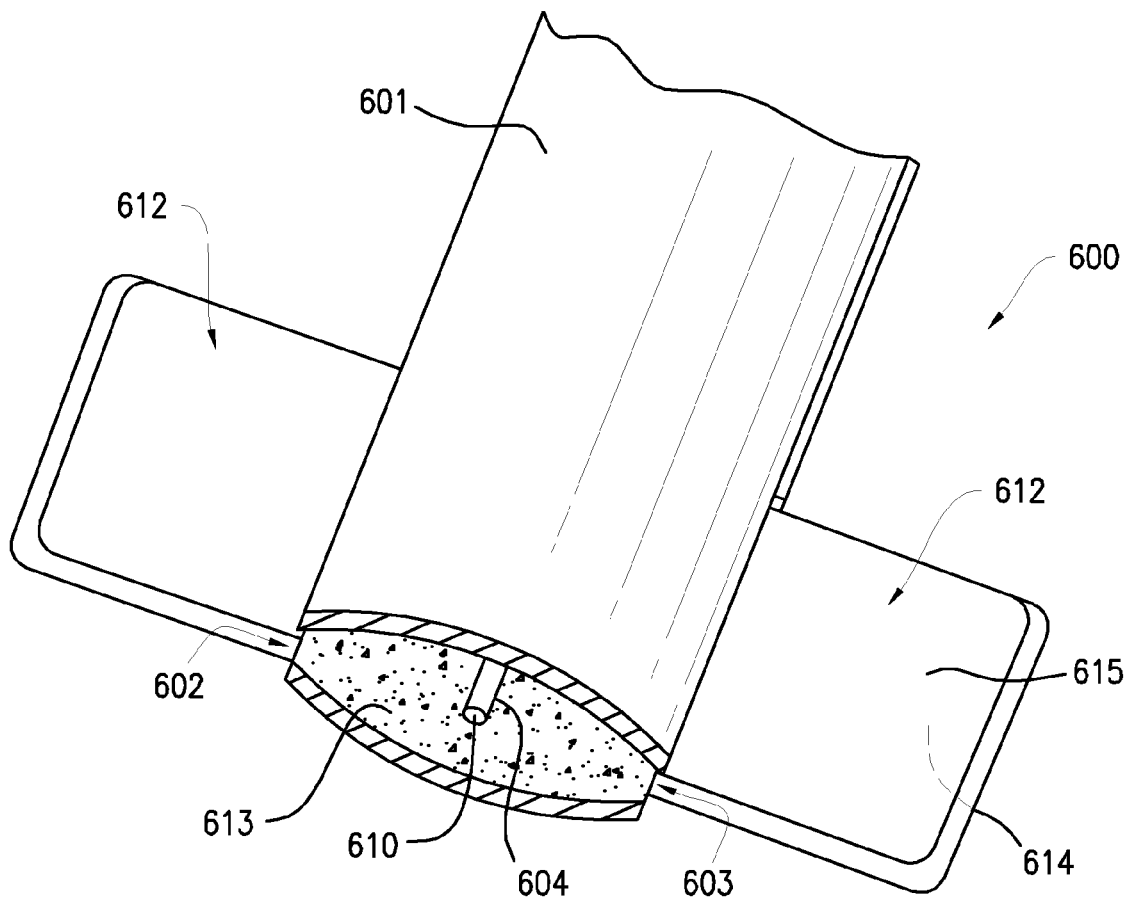

Referring to FIG. 8B, electrically conductive fluid 613 is delivered through distal opening 610 of fluid passage 604 into the balloon 612, thereby expanding balloon 612 through lateral openings 602, 603 of electrode shaft 601. In this configuration, balloon 612 extends to either side of electrode shaft 601 such that a surface 614 of balloon 612 (shown on the underside of balloon in FIG. 8B) is positioned in contact with or adjacent the target region of the dura. In an exemplary embodiment, balloon 612 is insulated on surface 615 opposite surface 614 to avoid unnecessary stimulation to other structures within the epidural space. Alternatively, device 600 may comprise multiple balloons with multiple fluid passages and electrodes. For example, the device may include two separate balloons that expand laterally outward in opposite directions from electrode shaft 601. In addition, it should be recognized that other configurations are possible. For example, balloon 612 may be positioned around the exterior of electrode shaft 601. In this embodiment, fluid passage 604 would extend along the exterior of shaft 601 and the balloon would be introduced into the patient in the deflated position.

As discussed above, a portion or all of surface 614 is preferably formed of an electrically-permeable material to allow for passage of an electrical impulse through outer surface 614. In a preferred embodiment, the material is ion-permeable (as described above) to allow for sufficient fluid to pass through outer surface 614 to wet the outer surface of the balloon. In this embodiment, balloon 612 is specifically designed to contact or, be positioned in close proximity to, a substantially larger surface area of the dura than conventional spinal cord stimulation electrode(s). Once in position, an electrical impulse (not shown) is then generated and applied to electrode shaft 601 and through outer surface 614 of balloon 612 to block or inhibit the pain signals in the dura. Alternatively, shaft 601 may comprise an insulating material (i.e., no electrode) and the electrical impulse can be applied directly through the conductive fluid to outer surface 614 of balloon 612 as described above.

In yet another embodiment, a system and method is disclosed to control the direction of an electric field applied to a target structure within or on a patient's body. In this embodiment, a device for applying energy to a patient's body includes multiple enclosures or balloons and multiple electrodes with different polarities. The device includes a source of electrical energy for applying electromagnetic fields or impulses to the electrodes and a fluid delivery system for delivering electrically conductive fluid to each of the balloons as described previously. The balloons are shaped and positioned to control the electric field between the two electrodes to specifically control the direction of the electric field applied to the target area of the patient.

Figure 9:
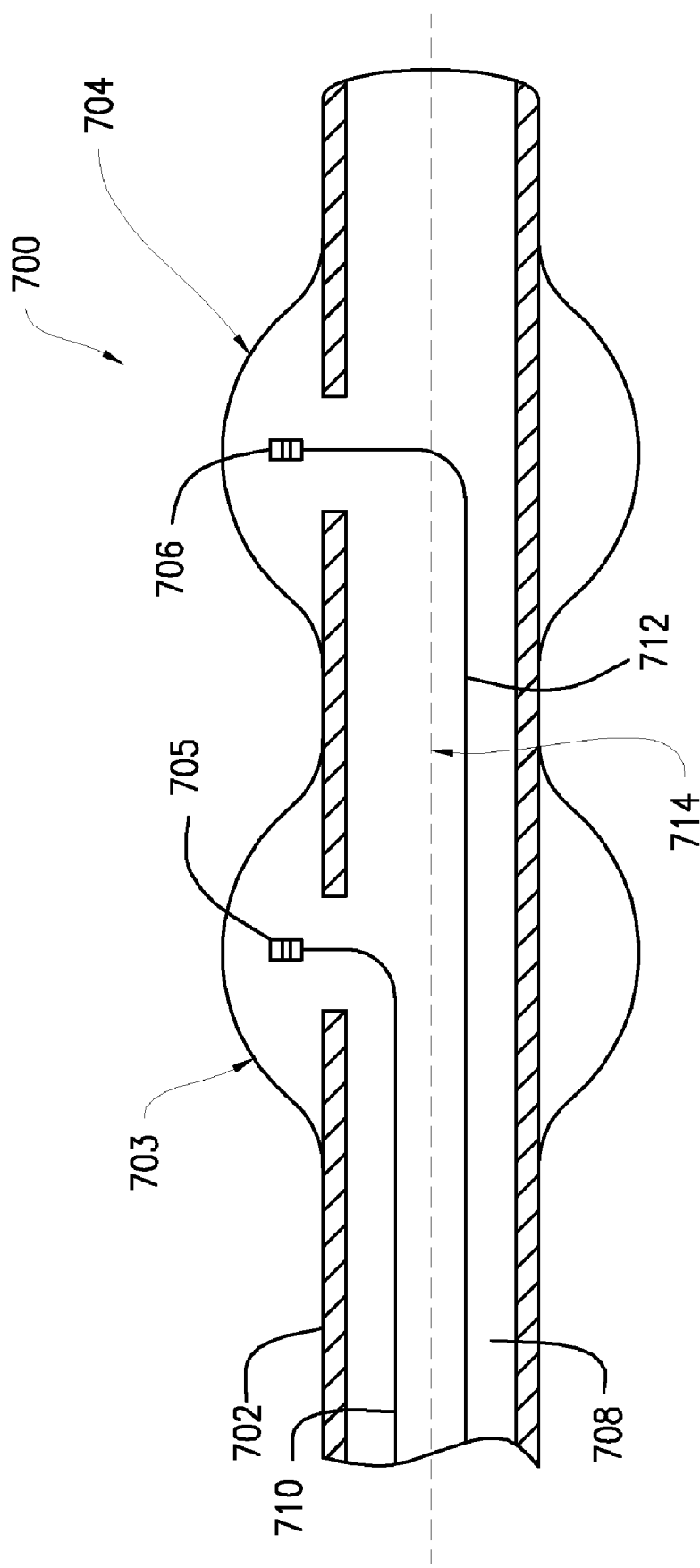
FIG. 9 illustrates another alternative embodiment of the present invention for stimulating nerves.

Referring to FIG. 9, an exemplary device 700 for applying a longitudinal or parallel electric field (not shown) to the longitudinal axis of a nerve fiber or axon (not shown) is illustrated. Nerve fibers are long slender projections of a nerve cell, or neuron, that conduct electrical impulses away from the neuron's cell body or soma. Nerve fibers or axons are the primary transmission lines of the nervous system and are typically sheathed in myelin. It is well known that an excitable tissue cell, such as a nerve fiber, is substantially less sensitive to a transverse electric field than a longitudinal electric field. Applying a longitudinal field increases the effect of this field on the excitable cell at the same frequencies, amplitudes, pulse durations and power levels.

In this embodiment, device 700 comprises an introducer shaft 702 having a longitudinal axis 701 and first and second balloons 703, 704 coupled to shaft 702. Introducer shaft 702 includes an internal lumen or fluid passage 708 fluidly coupled to a source of electrically conductive fluid and the interior of balloons 703, 704. Device 700 further includes first and second electrodes 705, 706 positioned within the interior of each of the balloons 703, 704 and electrically coupled to a source of electrical energy (not shown) by insulated conductors 710, 712, respectively. Electrodes 705, 706 are each spaced from the outer walls of the balloons 703, 704 in a similar manner as described above.

In use, shaft 702 is introduced into a target area within a patient, such as a nerve fiber, in manners well known in the art, such that longitudinal axis 701 of shaft 702 is substantially parallel to the nerve fiber. Conductive fluid (not shown) is delivered through fluid passage 708 to the interiors of balloons 703, 704 to inflate balloons 703, 704 such that the outer surfaces of balloons 703, 704 are in contact with, or adjacent to, the nerve fiber. The outer surfaces of balloons 703, 704 have one or more sections that are formed from an electrically-permeable material, preferably an ion-permeable material, to allow for electric impulses and fluid to pass through these sections of the balloons as described in detail above. Fluid passage 708 includes an inner section 714 between the interiors of each balloon 703, 704 that has a resistance to current greater than the resistance that will be encountered by the current as it passes from electrodes 705, 706, through the conductive fluid and the balloons 703, 704 and the adjoining space or tissue therebetween. Thus, the electric impulses or current preferably travel from electrodes 705, 706 through the conductive fluid and the outer surfaces of balloons 703, 704 to the nerve fiber. In the exemplary embodiment, this higher resistance in section 714 is accomplished by reducing the diameter of section 714 such that the electric resistance in this section is increased. In alternatively embodiments, device 700 may include an insulator (now shown) in inner section 714 of fluid passage 708 to substantially insulate the interior of the balloons from each other. In this alternative embodiment, the device 700 may include multiple fluid passages (i.e., one to each balloon).

Upon inflation of balloons 703, 704, a suitable electrical voltage/current profile for a stimulating, blocking and/or modulating impulse is applied to electrodes 705, 706 from the source of electrical energy, such as a pulse generator. The impulse signal generates an electric field (not shown) between electrodes 705, 706 that is substantially parallel to longitudinal axis 701 of shaft 702 and thus substantially parallel to the nerve fiber to block and/or modulate signals passing through the nerve fiber. It will be recognized by those skilled in the art that other configurations of the invention are possible. By way of example, the electric field can be controlled by insulating certain portions of the outer walls of balloons 703, 704 such that the electric field does not pass through such insulated portions.

Figure 10:
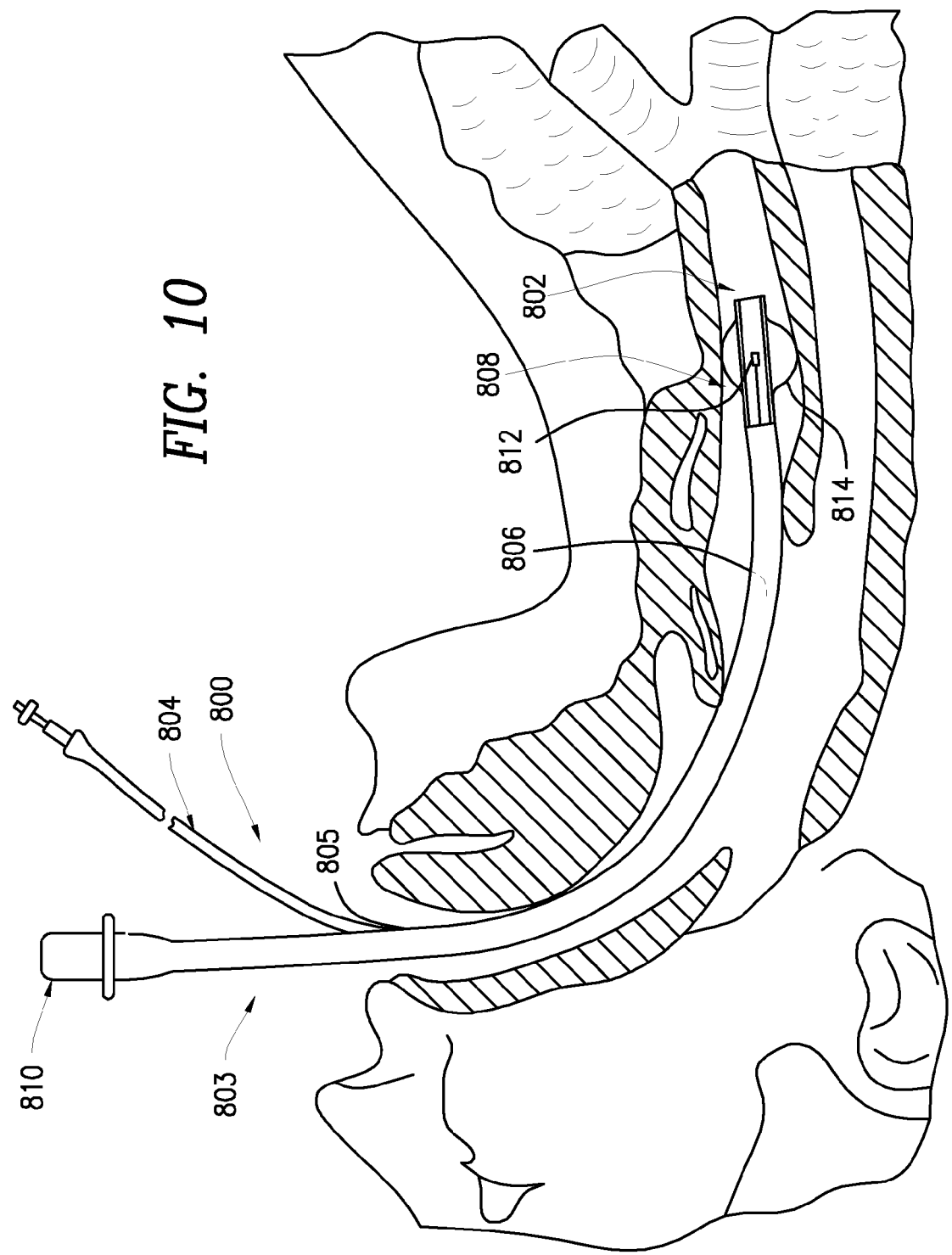
FIG. 10 illustrates another alternative embodiment of the present invention for use in a patient's trachea.

Referring now to FIG. 10, an alternative embodiment is illustrated for treatment of the vagus nerve with a device 800 introduced through the trachea 802 of a patient. As shown, device 800 includes an endotracheal tube 803 that is inserted into the patient under intubation as is well known in the art. Tube 803 comprises a flexible shaft 805 with an inner lumen 806, and a distal balloon electrode device 808. Note that balloon electrode device 808 may be an integral part of tube 803 or it may be a separate device that is inserted through the inner lumen 806 of a standard endotracheal tube. Many types of conventional endotracheal tubes may be used, such as oral un-cuffed, oral cuffed, Rae tube, nasal tube, reinforced tube, double-lumen tubes and the like. Tube 803 also includes a fluid passage 804 fluidly coupling the inner lumen 806 with a source of electrically conductive fluid (not shown) and a proximal port 810 for coupling to a source of electrical energy (also not shown). Tube 802 may also include an aspiration lumen (not shown) for aspirating the conductive fluid and/or other bodily fluids as is well known in the art.

As described previously, balloon electrode device 808 includes an electrode 812 positioned within the interior of a balloon 814. Electrode 812 is preferably a single negative electrode. A return electrode (not shown) consisting of an EKG-like electrode with a sticky, conductive surface is placed at any convenient location on the exterior of the patient's body. Alternatively, the signal may be applied through a pair of bipolar electrodes within the tracheal tube 803, preferably positioned 1 to 10 cm apart from each other at a location of about 10 to 30 cm from the mouth or nasal openings. The interior of balloon 814 is fluidly coupled to the fluid passage 804 for delivery of electrically conductive fluid into the balloon 814. Balloon 814 is sized and shaped such that, when inflated with the conductive fluid, it will contact, or come in close proximity with, the inner walls of the patient's trachea 802.

In use, an electrical stimulation signal is applied to electrode 812 such that electrical impulses travel from electrode 812 through the conductive fluid and the balloon 814 to the tracheal tissue. Applicant has discovered a unique electrical signal that will rapidly cause bronchodilation when applied from the lumen of the patient's trachea. The optimal signal consists of voltage pulses, 200 us in duration (range 50 to 500 us), repeated at 25 Hz (range 10 to 50 Hz) with an amplitude of 7 V (range 1 to 15 V). This signal has been shown in a pig model of histamine induced bronchoconstriction to rapidly and potently inhibit both acute and chronic air way pressure elevation.

In another embodiment, the invention may be useful for delivering an agent, such as a drug, to a target location within a patient. In an exemplary embodiment, the invention can be used for the treatment of cancer, such as esophageal, lung, prostate, colon or other cancers, by filling the balloon with a charged anti-cancer drug and then positioning the balloon adjacent to, or into, a tumor with the appropriate polarity stimulation. In this embodiment, the conductive fluid, balloon material and electric signal generated to the electrode are selected in combination to allow for passage of the agent or drug through the pores of the balloon and into the tissue. For example, the balloon may be formed of a material having a pore size that will permit the passage of certain drugs, such as anti-cancer agents, through the outer wall of the balloon. In this manner, the balloon may act as a drug-delivery device by introducing one or more drugs into the conductive fluid and permitting the drug(s) to pass through the balloon and into the tissue. Moreover, the device may be used to time-release the drugs into the patient's tissue.

In an exemplary embodiment, an introducer is designed for introducing the balloon-electrode device to the target site within the patient either percutaneously, endoscopically or through an open procedure. The introducer will include a conductor coupled to the electrode and a source of electrical energy, a fluid passage coupled to the interior of the balloon for delivering conductive fluid and a drug to the balloon, and an aspiration passage for aspirating the conductive fluid. The conductive fluid is continuously circulated from the fluid passage through the interior of the balloon to the aspiration passage to precisely control the dosage of drugs delivered into the patient over a period of time. In alternative embodiments, the full drug dose may be delivered into the balloon at one time, and the material of the balloon and/or electric field and conductive fluid are configured to allow for passage of the drug through its outer wall over a period of time.

In another embodiment, the present invention may be used for treating the temporary arrest of intestinal peristalsis as described more fully in commonly assigned U.S. patent application Ser. No. 12/246,605, which has already been incorporated herein by reference. In this embodiment, a balloon electrode device as described above is introduced into the patient and placed in contact with, or close proximity to, at least one of the celiac ganglia, cervical ganglia and thoracic ganglia of the sympathetic nerve chain. An electric signal is applied to the electrode and/or balloon to induce at least one of an electric current, an electric field and an electromagnetic field in the sympathetic nerve chain to modulate and/or block inhibitory nerve signals thereof such that intestinal peristalsis function is at least partially improved. Alternatively or additionally, the electric current, electric field and/or electromagnetic field may be applied to at least a portion of the splanchnic nerves of the sympathetic nerve chain, and/or the spinal levels from T5 to L2.

In one aspect of this embodiment, the balloon electrode may be introduced through the trachea of a patient during surgery. For example, the balloon electrode device may be attached to an endotracheal tube such as the one illustrated in FIG. 10 and discussed in more detail above. In this embodiment, an electric impulse is delivered to the vagus nerve during surgery to stimulate, block and/or modulate nerves signals thereof to either prevent peristalsis function from becoming impaired during the surgery or to immediately improve such function after it becomes impaired as a result of the surgery. Alternatively, the balloon electrode may be attached to an NG tube (as described above) and introduced into the patient's esophagus after the surgery is completed. In this manner, the electric impulse may be applied during or almost immediately after surgery before the patient's peristalsis function has been impaired or before the symptoms of such disfunction significantly impact the patient.

Alternatively, the balloon electrode may be introduced into the epidural space of the patient after the surgery has been completed. As described more fully above, the balloon electrode is preferably introduced through a small portal and then expanded inside the epidural space to achieve a larger footprint of contact on the dura. This ensures that the electric impulse will target the selected nerves to sufficiently influence the therapeutic result. In addition, it inhibits migration of the electrode within the epidural space and provides for a more efficient and effective treatment.

As described more fully in the Ser. No. 12/246,605 patent application, drive signals may be applied to the one or more electrodes (or directly to the fluid within the balloon) to produce the at least one impulse and induce the current and/or field(s). The drive signals may include at least one of sine waves, square waves, triangle waves, exponential waves, and complex impulses. The drive signals inducing the current and/or fields preferably have a frequency, an amplitude, a duty cycle, a pulse width, a pulse shape, etc. selected to influence the therapeutic result, namely modulating some or all of the nerve transmissions in the sympathetic nerve chain. By way of example, the parameters of the drive signal may include a square wave profile having a frequency of about 10 Hz or greater, such as between about 15 Hz to 200 Hz, and more preferably between about 15 Hz to about 50 Hz. The drive signal may include a duty cycle of between about 1 to 100%. The drive signal may have a pulse width selected to influence the therapeutic result, such as about 20 us or greater, such as about 20 us to about 1000 us. The drive signal may have a peak voltage amplitude selected to influence the therapeutic result, such as about 0.2 volts or greater, such as about 0.2 volts to about 20 volts.

In yet another embodiment, the invention may be useful for blocking pain transmission associated with surgeries or other events, such as dental surgery. In this embodiment, a balloon electrode device as described above is introduced to a location adjacent the target nerve and an appropriate electrical signal is applied to the electrode to block the pain signals generated by the nerve. In one aspect of this embodiment, the electrode is introduced through the nose and placed in the back of the throat to block pain transmissions during dental surgery as an alternative to lidicaine injections.

In yet another embodiment of the present invention, a device for mild brain stimulation is disclosed. Recent studies have indicated that motor skill learning may be enhanced by applying a mild electrical current to a motor control area of the brain (see study conducted by the National Institute of Health and presented in the Jan. 20, 2009 early online edition of the Proceedings of the National Academy of Sciences). Patients receiving this current were significantly better able to learn and perform a complex motor task than those in the control groups. The findings could hold promise for enhancing rehabilitation for people with traumatic brain injury, stroke and other conditions. Motor skills which are used for activities from typing to driving, to sports, require practice and learning over a prolonged period of time. During practice, the brain encodes information about how to perform the task, but even during periods of rest, the brain is still working to strengthen the memory of doing the task. This process is known as consolidation. During practice, one group received 20 minutes of transcranial direct current stimulation (tDCS), which involves mild electrical stimulation applied through surface electrodes on the head, and works by modulating the excitability of cells in the brain's outermost layers, such as the primary motor cortex.

One of the limitations of current tDCS is that the direct current can only be applied for a limited period of time and at a limited power or voltage because the electrodes will begin to damage the tissue they are in contact with. The present invention solves this problem by providing a balloon electrode device having two balloons configured for placement on the outer surface of the patient's head. The device further includes two electrodes of opposite polarity positioned within the interior of the balloons. The balloons are coupled to a source of conductive fluid and a source of electrical energy, as described above. In use, conductive fluid is delivered to the interior of the balloons to inflate the balloons such that the electrodes are substantially centered within their interiors. As described above, direct current is then applied to the electrodes. The direct current flows through the conductive fluid and the outer surfaces of the balloons into the patient's brain, as is described in the art.

Since the electrodes do not directly contact the tissue of the patient, the present invention reduces the potential for collateral tissue damage or necrosis and/or excessive electric fields in the tissue. In addition, the balloons physically shield the electrode from the tissue of the patient's head, which substantially inhibits Faradic products (e.g., $OH^-$, $H_2O_2$) of the electrodes from contacting this tissue. Thus, the direct current can be applied to the patient's brain without the danger of such Faradic products reaching excessively high concentrations at the tissue site, allowing for a longer treatment time and/or higher current levels than is currently considered safe for the patient.

In another embodiment of the invention, an improved nerve cuff is disclosed. Electrical stimulation of nerve fibers has been extensively studied in an effort to either activate muscles associated with the target nerves, modulate nerve transmissions, accelerate growth of the nerve fibers to repair severed fibers and the like. Typically, nerve cuffs are wrapped around the nerve and provided with a number of discrete electrodes in the form of surface electrodes that can contact the nerve, i.e., the surface of the peripheral nerve trunk, at different positions. Electrical impulses can be delivered to the electrodes to stimulate or activate nerve fascicles in the nerve trunk, whereby muscles may be activated, nerve transmission may be modulated and/or the nerve fiber growth can be accelerated.

In this embodiment, a nerve cuff device is provided comprising a substantially annular shaft designed for wrapping around a target nerve fiber. The annular shaft includes one or more balloons configured for inflation such that the balloon contacts the circumferential surface of the nerve fiber. One or more electrodes are positioned within the interior of the balloon(s) and spaced from the outer walls of the balloon(s). As described previously, the electrodes are coupled to a source of electrical energy for delivering electrical impulses to the interior of the balloons. The balloons are fluidly coupled to a source of electrically conductive fluid as described previously.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for delivering energy to a mammal, comprising:
   an enclosure having an outer wall surrounding an interior, the outer wall having at least one section that is formed from an electrically-permeable material and a fluidly-permeable material;
   an electrode within the interior of the enclosure spaced from the electrically-permeable section of the outer wall; and
   a fluid passage coupled to the interior of the enclosure for delivery of an electrically conductive fluid into said interior such that the electrically conductive fluid couples the electrode with the electrically-permeable section of the outer wall.

2. The device of claim 1 wherein the enclosure is expandable.

3. The device of claim 1 wherein the enclosure is a balloon.

4. The device of claim 3 wherein the balloon is movable between a deflated position for introduction into a patient and an inflated position for contacting said tissue within the patient.

5. The device of claim 1 wherein the electrode is substantially centrally located within the enclosure.

6. The device of claim 1 wherein said section of the outer wall is formed of an ion-permeable material.

7. The device of claim 1 wherein said section of the outer wall is formed from a fluidly-permeable material.

8. The device of claim 1 wherein the outer wall is formed of a material substantially conformable to tissue.

9. The device of claim 3 wherein the balloon is elastic.

10. The device of claim 1 further comprising a nasogastral (NG) tube having an internal passageway and an external surface, wherein the electrode is coupled to the external surface of the NG tube within the interior of the enclosure.

11. The device of claim 10 further comprising a conductor extending through the internal passageway of the NG tube and electrically coupled to the electrode.

12. The device of claim 1, wherein the electrode is generally cylindrically-shaped.

13. The device of claim 1, wherein electrical properties of the electrode, the electrically conductive fluid, and the electrically-permeable material of the enclosure are such that a resistance through the electrode, the electrically conductive fluid, and the electrically-permeable material of the enclosure is no more than about 200 Ohms.

14. The device of claim 1, wherein the electrically conductive fluid is about 5% saline solution.

15. The device of claim 1, further comprising an electrical signal generator operating to apply at least one electrical signal to the electrode such that, when the enclosure is positioned in an esophagus of the mammal, an electro-magnetic field emanates from the electrode to at least one of nerves and muscles in a vicinity of the esophagus of the mammal.

16. The device of claim 15, further comprising a return electrode adapted for contact with the mammal, wherein the electrode and the return electrode are adapted such that the electro-magnetic field emanating from the electrode is in a substantially radial pattern.

17. The device of claim 1, wherein the enclosure is sized and shaped such that it operates to: (i) slide, in a deflated state, past a cricoid cartilage of the mammal, and (ii) seat, when in an inflated state, when slid back toward the cricoid cartilage.

18. The device of claim 15 wherein the electrical signal generator operates such that the at least one electrical signal is of a frequency between about 1 Hz to 3000Hz, a pulse duration of between about 10-1000 us, and an amplitude of between about 1-20 volts.

19. A system for delivering energy to a mammal comprising:
   a source of electrical energy;
   an enclosure coupled to the source of electrical energy and having an outer wall surrounding an interior; the outer wall having at least one section that is formed of an electrically-permeable material; and
   a fluid delivery device fluidly coupled to the interior of the enclosure for delivering electrically conductive fluid to said interior such that the electrically-permeable section of the outer wall is electrically coupled to the electrical energy source; and wherein said section is fluidly-permeable such that the electrically conductive fluid wets an outer surface of said section when the balloon is in the inflated position.

20. The system of claim 19 further comprising an introducer having an internal passageway and an external surface within the interior of the enclosure such that when the enclosure is inflated with conductive fluid, the fluid acts as an electrode within the interior of the enclosure.

21. The system of claim 20 wherein the introducer is an NG tube comprising a conductor extending through the internal passageway of the NG tube to provide a path for electrical current to flow to the fluid within the balloon.

22. The system of claim 19 wherein the enclosure is a balloon movable between a deflated position for introduction into a patient and an inflated position for contacting tissue within the patient.

23. The system of claim 22 wherein the electrode is substantially centrally located within the enclosure in the inflated position.

24. A method of treating an ailment in a mammal comprising:
    inserting an enclosure in a deflated state into an esophagus distal to a cricoid cartilage of the mammal;
    contacting a tissue of the esophagus of the mammal with an electrically-permeable portion of an outer wall of the enclosure;
    applying electrical energy to an electrode within the enclosure; and
    delivering electrically conductive fluid into the enclosure such that the conductive fluid electrically couples the electrode with the electrically-permeable portion of the outer wall of the enclosure;
    inflating the enclosure such that the electrically-permeable portion of the outer wall contacts the tissue; and
    extracting the enclosure proximally towards to the cricoid cartilage.

25. The method of claim 24 further comprising inflating the enclosure with the electrically conductive fluid such that the electrode is substantially centrally located within an interior volume of the enclosure.

26. The method of claim 24 wherein the applying step is carried out by applying at least one electrical signal to the electrode such that an electro-magnetic field emanates from the electrode to at least one of nerves and muscles of the mammal.

27. The method of claim 26 further comprising modulating nerve signals within the vagus nerve of the mammal.

28. The method of claim 26 further comprising reducing the magnitude of constriction of bronchial smooth muscle of the mammal during the applying step.

29. The method of claim 26 further comprising increasing a blood pressure of the mammal during the applying step.

30. The method of claim 26 further comprising decreasing a blood pressure of the mammal during the applying step.

31. The method of claim 24, further comprising contacting a return electrode to an external portion of the mammal and emanating an electro-magnetic field from the electrode through the tissue in a substantially radial pattern.

32. The method of claim 24 wherein electrical properties of the electrode, the conductive fluid, and the electrically-permeable portion of the enclosure are such that a resistance through the electrode, the conductive fluid, and electrically-permeable portion of the enclosure is no more than about 200 Ohms.

33. The method of claim 24 wherein the applying step is carried out by applying an electrical signal to the electrode of a frequency between about 1 Hz to 3000 Hz, a pulse duration of between about 10-1000 us, and an amplitude of between about 1-20 volts.

34. The method of claim 24 further comprising evacuating the conductive fluid from the interior of the enclosure.

35. The method of claim 34 wherein the evacuating step is carried out simultaneously with the delivering step.

36. The method of claim 24 further comprising delivering an agent into the interior of the balloon with the conductive fluid such that the agent passes through the outer wall of the enclosure to the tissue.

37. The method of claim 36 wherein the agent is an anti-cancer drug.

38. The method of claim 36 wherein the agent is an antiseptic drug, such as silver.

* * * * *